(12) United States Patent
Margolskee

(10) Patent No.: US 9,012,161 B2
(45) Date of Patent: Apr. 21, 2015

(54) METHODS OF IDENTIFYING MOLECULES THAT PROVIDE OR ENHANCE SWEET TASTE

(75) Inventor: Robert Franklin Margolskee, Voorhees, NJ (US)

(73) Assignee: Monell Chemical Senses Center, Philadelphia, PA (US)

( * ) Notice: Subject to any disclaimer, the term of this patent is extended or adjusted under 35 U.S.C. 154(b) by 0 days.

(21) Appl. No.: 13/978,462

(22) PCT Filed: Jan. 17, 2012

(86) PCT No.: PCT/US2012/021498
§ 371 (c)(1),
(2), (4) Date: Jul. 5, 2013

(87) PCT Pub. No.: WO2012/102900
PCT Pub. Date: Aug. 2, 2012

(65) Prior Publication Data
US 2013/0280371 A1 Oct. 24, 2013

Related U.S. Application Data

(60) Provisional application No. 61/435,904, filed on Jan. 25, 2011.

(51) Int. Cl.
*G01N 33/567* (2006.01)
*G01N 33/53* (2006.01)
*G01N 33/50* (2006.01)
*G01N 33/68* (2006.01)

(52) U.S. Cl.
CPC .......... *G01N 33/502* (2013.01); *G01N 33/5008* (2013.01); *G01N 33/6872* (2013.01)

(58) Field of Classification Search
None
See application file for complete search history.

(56) References Cited

U.S. PATENT DOCUMENTS

| 6,166,076 | A | 12/2000 | Gilbertson |
| 2003/0148421 | A1 | 8/2003 | Newgard |
| 2004/0098757 | A1 | 5/2004 | Seino |
| 2008/0050756 | A1 | 2/2008 | Kim |
| 2009/0306212 | A1 | 12/2009 | Polak |

FOREIGN PATENT DOCUMENTS

EP 1347047 1/2011

OTHER PUBLICATIONS

Edwards G. and Weston AH. Cardiovascular Drugs and Therapy 9:185-192, 1995.*
Baukrowitz et al, "PIP2 and PIP as Determinants for ATP Inhibition of KATP Channels", Science, vol. 282 (5391):1141-1144, Nov. 6, 1998.
International Search Report for PCT/US2012/021498 dated May 11, 2012.
International Written Opinion for PCT/US2012/021498 dated May 11, 2012.
Bartoshuk, L.M., et al, Sweet taste of dilute NaCl: psychophysical evidence for a sweet stimulus. Physiol Behav. Oct. 1978; 21 (4):609-13.
Bartoshuk, L.M., et al, Taste of Sodium Chloride Solutions After Adaptation To Sodium Chloride: Implications For The "Water Taste". Science. Feb. 28, 1964; 143:967-8.
Dubois, G.E., et al, Concentration-response relationships of sweeteners: A systematic study. In: Walters DE, et al, eds. Sweeteners: Discovery, molecular design, and chemoreception. American Chemical Society: 1991: 261-276.
Kinnamon, S.C.; Margolskee, R.F. (2008) Taste Transduction. The Senses: A Comprehensive Reference. Ed R.R. Hoy, G.M Shepherd, A.I. Basbaum, A. Kaneko and G. Westheimer. vol. 2.
Kitawaga, M. et al. Molecular genetic identification of a candidate receptor gene for sweet taste. Biochem Biophys Res Commun. Apr. 27, 2001; 283 (1): 236-42.
Liu, D.X., et al. Expression of sulfonylurea receptors in rat taste buds. Acta Histochem. Jun. 30, 2010. [Epub ahead of print].
Max, M., et al. Tas1r3, encoding a new candidate taste receptor, is allelic to the sweet responsiveness locus Sac. Nat Genet. May 2001; 28(1):58-63.
Montmayeur, J.P., et al. A candidate taste receptor gene near a sweet taste locus. Nat Neurosci. May 2001; 4(5):492-8.
Nichols, C.G., KATP channels as molecular sensors of cellular metabolism. Nature. Mar. 23, 2006; 440(7083):470-6. Review.
Pelz, W.E., et al. Genetic influences on saccharin preference of mice. Physiol Behav. Feb. 1973; 10(2):263-5.
Reed, D.R., et al. Heritable variation in food preferences and their contribution to obesity. Behav Genet. Jul. 1997; 27(4):373-87. Review.
Scheepers, A., et al. The glucose transporter families SGLT and GLUT: molecular basis of normal and aberrant function. JPEN J Parenter Enteral Nutr. Sep.-Oct. 2004; 28(5):364-71. Review.
Schiffman, S.S., et al, Multiple receptor sites mediate sweetness: evidence from cross adaptation. Pharmacol Biochem Behav. Sep. 1981; 15(3):377-88.
Simon, S.A., et al. Activation by saccharides of a cation-selective pathway on canine lingual epithelium. Am J Physiol. Feb. 1989; 256(2 Pt 2):R394-402.
Simon, S.A., (1991) Mechanisms of Sweet Taste Transduction in Sweeteners, ACS Symposium Series, vol. 450, pp. 237-250.
Winnig, M., et al. Valine 738 and lysine 735 in the fifth transmembrane domain of rTas1r3 mediate insensitivity towards lactisole of the rat sweet taste receptor. BMC Neurosci. Apr. 7, 2005; 6:22.

(Continued)

*Primary Examiner* — Robert Landsman
(74) *Attorney, Agent, or Firm* — Howson & Howson LLP

(57) ABSTRACT

The present invention provides methods for identifying a molecule that provides or enhances a sweet taste in the mouth and compositions containing such molecules. The methods involve determining the effect of a variety of known or new compounds on expression or functional activity of a glucose-transporter protein of the activity of an ATP-gated K+ channel ($K_{ATP}$) in a mammalian oral cell, taste cell, or heterologous cell that expresses the protein or channel.

15 Claims, 3 Drawing Sheets

(56) References Cited

OTHER PUBLICATIONS

Zhao, G.Q., et al. The receptors for mammalian sweet and umami taste. Cell. Oct. 31, 2003; 115(3):255-66.

Wilson-O'Brien, A., et al, Mitogen-stimulated and rapamycin-sensitive glucose transporter 12 targeting and functional glucose transport in renal epithelial cells. Endocrinology, Mar. 2008; 149(3):917-24. Epub Nov. 26, 2007.

Amico, J.A et al, "Enhanced initial and sustained intake of sucrose solution in mice with an oxytocin gene deletion", Am J Physiol Regul Integr Comp Physiol, Dec. 2005; 289(6): R1798-806. Epub Sep. 8, 2005.

Bachmanov, A.A.; Beauchamp G.K., "Taste receptor genes", Annu Rev Nutr, 2007; 27:389-414.

Bachmanov, A.A. et al, "Positional cloning of the mouse saccharin preference (Sac) locus", Chem Senses, Sep. 2001; 26(7):925-33.

Bachmanov A.A. et al, "Sucrose consumption in mice: major influence of two genetic loci affecting peripheral sensory responses", Mamm Genome, Aug. 1997; 8(8):545-8.

Baquero A.F.; Gilbertson T.A., "Insulin activates epithelial sodium channel (ENaC) via phosphoinositide 3-kinase in mammalian taste receptor cells", Am J Physiol., Apr. 2011; 300(4): C860-C871. Epub Nov. 2010.

Clapp T.R. et al, "Mouse taste cells with G protein-coupled taste receptors lack voltage-gated calcium channels and SNAP-25", BMC Biol, Mar. 2006; 4:7.

Damak S, et al, "Detection of sweet and umami taste in the absence of taste receptor T1r3", Science, Aug. 2003; 301(5634):850-3. Epub Jul. 17, 2003.

Delay E.R., et al, "Sucrose and monosodium glutamate taste thresholds and discrimination ability of T1R3 knockout mice", Chem Senses, May 2006; 31(4):351-7. Epub Feb. 22, 2006.

Desimone J.A. et al, "The active ion transport properties of canine lingual epithelia in vitro. Implications for gustatory transduction", J Gen Physiol, May 1984; 83(5):633-56.

Dubois G.E.; Lee J.F., "A simple technique for the evaluation of temporal taste properties", Chem. Senses, 1983 7 (3-4): 237-247.

Fuller J.L., "Single-locus control of saccharin preference in mice", J. Hered, Jan.-Feb. 1974; 65(1):33-6.

Fushan, A.A., et al, "Association between common variation in genes encoding sweet taste signaling components and human sucrose perception", Chem Senses, Sep. 2010; 35(7):579-92. Epub Jul. 21, 2010.

Fushan, A.A., et al, "Allelic polymorphism within the TAS1R3 promoter is associated with human taste sensitivity to sucrose", Curr Biol. Aug. 11, 2009;19(15):1288-93. Epub Jun. 25, 2009.

Hevezi P, et al, "Genome-wide analysis of gene expression in primate taste buds reveals links to diverse processes", PLoS One. Jul. 28, 2009; 4(7):e6395.

Jiang P, et al, "Lactisole interacts with the transmembrane domains of human T1R3 to inhibit sweet taste", J. Biol Chem. Apr. 15, 2005;280(15):15238-46. Epub Jan. 24, 2005.

Jyotaki M, et al, "Modulation of sweet taste sensitivity by orexigenic and anorexigenic factors", Endocr J. 2010; 57(6):467-75. Epub Apr. 23, 2010. Review.

Keskitalo K, et al, "Sweet taste preferences are partly genetically determined: identification of a trait locus on chromosome 16", Am J Clin Nutr. Jul. 2007; 86(1):55-63.

Kumazawa T.; Kurihara K., "Large enhancement of canine taste responses to sugars by salts", J. Gen Physiol. May 1990; 95(5):1007-18.

Li X, et al, "Human receptors for sweet and umami taste", Proc Natl Acad Sci U S A. Apr. 2, 2002; 99(7):4692-6. Epub Mar. 26, 2002.

McTaggart JS, et al, "The role of the KATP channel in glucose homeostatis in health and disease: more than meets the islet", J Physiol. Sep. 1, 2010; 588(Pt 17):3201- 9. Epub Jun. 2, 2010.

Mierson S, et al, "Sugar-activated ion transport in canine lingual epithelium. Implications for sugar taste transduction", J. Gen Physiol. Jul. 1988; 92(1):87-111.

Nelson G, et al, "Mammalian sweet taste receptors", Cell. Aug. 10, 2001; 106(3):381- 90.

Quesada I, et al, "Nuclear KATP channels trigger nuclear Ca(2+) transients that modulate nuclear function", Proc Natl Acad Sci U S A. Jul. 9, 2002; 99(14):9544-9. Epub Jun. 27, 2002.

Sainz E, et al, "Identification of a novel member of the T1R family of putative taste receptors", J Neurochem. May 2001; 77(3):896-903.

Sclafani, A, et al, "Oxytocin knockout mice demonstrate enhanced intake of sweet and nonsweet carbohydrate solutions", Am J Physiol Regul Integr Comp Physiol. May 2007; 292(5):R1828-33. Epub Feb. 1, 2007.

Shigemura N. et al, "Leptin modulates behavioral responses to sweet substances by influencing peripheral taste structures", Endocrinology. Feb. 2004; 145(2):839-47. Epub Oct. 30, 2003.

Shin Y.K., et al, "Modulation of taste sensitivity by GLP-1 signaling", J Neurochem. Jul. 2008; 106(1):455-63. Epub Jul. 1, 2008.

Ugawa T. et al, "Enhancing effects of NaCl and Na phosphate on human gustatory responses to amino acids", Chem Senses 1992 17 (6):811-815.

Xu, H. et al, "Different functional roles of T1R subunits in the heteromeric taste receptors", Proc Natl Acad Sci U S A. Sep. 28, 2004; 101(39):14258-63. Epub Sep. 7, 2004.

Yoshida R. et al, "Endocannabinoids selectively enhance sweet taste", Proc Natl Acad Sci U S A. Jan. 12, 2010; 107(2):935-9. Epub Dec. 22, 2009.

Zhao F.Q.; Keating A.F., "Functional properties and genomics of glucose transporters", Curr Genomics. Apr. 2007; 8(2):113-28.

Busch, J. et al, "Temporal Contrast of Salt Delivery in Mouth Increases Salt Perception", Chem. Senses 34: 341-348, Mar. 2009.

Fudge, M. et al, "Tamoxifen produces conditioned taste avoidance in male rats: An analysis of microstructural licking patterns and taste reactivity", Horm Behav. Sep. 2009; 56(3): 322-331.

Ayestaran, A. et al, "Toxic but Drank: Gustatory Aversive Compounds Induce Post-ingestional Malaise in Harnessed Honeybees", PLoS One Oct. 27, 2010; 5(10):e15000.

Shetty, M. et al, "Rapid Activation of GLUT-1 Glucose Transporter following Inhibition of Oxidative Phosphorylation in Clone 9 Cells", J. Biol. Chem. Mar. 1993, 268(23): 17225-17232.

Stevens, J.M. et al, "Tumor necrosis factor alpha-induced glucose transporter (GLUT-1) mRNA stabilization in 3T3-L1 preadipocytes. Regulation by the adenosine-uridine binding factor", J. Biol. Chem. 1992, 267: 8336-8341.

Turner, J. et al, "Carboxyl-terminal Vesicular Stomatitis Virus G Protein-tagged Intestinal Na-dependent Glucose Cotransporter (SGLT1): Maintenance of Surface Expression and Global Transport Function With Selective Perturbation of Transport Kinetics and Polarized Expression", J. Biol. Chem. 1996, 271:7738-7744.

International Preliminary Report on Patentability for corresponding PCT/US2012/021498, mailed Aug. 8, 2013.

Gilbertson et al, The physiology of vertebrate taste reception, Current Opinion in Neurobiology, 3(4):532-9 (Aug. 1993).

Office Action dated Aug. 8, 2014 issued in corresponding Chinese patent application No. 201280006363.5.

* cited by examiner

METHODS OF IDENTIFYING MOLECULES THAT PROVIDE OR ENHANCE SWEET TASTE

CROSS-REFERENCE TO RELATED APPLICATIONS

This application is a national stage of International Patent Application No. PCT/US2012/021498, filed Jan. 17, 2012, which claims the benefit of the priority of U.S. Provisional Patent Application No. 61/435,904, filed Jan. 25, 2011, which applications are incorporated herein by reference.

BACKGROUND OF THE INVENTION

A broad array of sweet compounds including monosaccharide and disaccharide sugars (glucose, fructose, sucrose), sugar alcohols, small molecule non-caloric sweeteners (saccharin, cyclamate, sucralose), dipeptides (aspartame, neotame), and protein sweeteners (monellin, thaumatin, brazzein) exist for use as food additives and to sweeten products from toothpaste to pharmaceutical preparations. However, it has been clear that humans have a preference for the naturally occurring sweeteners over the artificial non-caloric sweeteners that have been developed over the years.

Prior to the molecular identification of the primary sweet taste sensor as a heterodimeric combination of two family C G protein coupled receptors (GPCRs), T1r2+T1r3 (reviewed in Bachmanov A A, Beauchamp, 2007), it had been proposed that sweet taste might rely on sugar transporters or sugar-gated cation channels (DeSimone J A, Heck G L, Mierson S, Desimone S K., 1984; Mierson S, DeSimone S K, Heck G L, DeSimone J A., 1988; Simon S A, Labarca P, Robb R., 1989; Simon S A, 1991). Glucose transporters (GLUT), sodium glucose co-transporters (SGLT) and $K_{ATP}$ metabolic sensors play important roles in glucose homeostasis and metabolism throughout the body and in many specific organs (e.g. gut, pancreas, heart, skeletal muscle, brain) (reviewed in Scheepers A, Joost H G, Schürmann A., 2004; McTaggart J S, Clark R H, Ashcroft F M., 2010; Nichols C G., 2006; Zhao and Keating, 2007). However, the presence and function in taste cells of these important proteins are largely unknown. Liu et al. (Acta Histochemica, 2010) identified SUR1 (a component of $K_{ATP}$) in rat fungiform taste cells, but found SUR1 to be absent from rat circumvallate taste cells. Liu et al did not examine taste cell type specific expression. Hevezi et al. (PLoS One, 2009) identified GLUT8, GLUT9, GLUT10, GLUT13, SLC2A4RG (a regulator of GLUT4) and the insulin receptor as genes potentially expressed in macaque taste cells/buds. However, these authors did not confirm the expression of these genes in taste cells or determine if they are expressed in specific types of taste cells.

SUMMARY OF THE INVENTION

In one aspect, a method of identifying a molecule that provides or enhances a sweet taste in the mouth is provided by screening for the effect of a test molecule on the expression or activity of a glucose-transporter protein in a cell. In one embodiment, this method involves contacting a test molecule with a mammalian cell or cell line that expresses a glucose-transporter protein under in vitro culture conditions; and measuring the expression level or functional activity of the glucose-transporter protein by the contacted cell or cell line. An increase in protein expression of the glucose-transporter protein or functional activity of the glucose-transporter protein by the cell or cell line contacted with the test molecule over that of a positive or negative control cell or cell line identifies a test molecule that provides or enhances a sweet taste.

In another aspect, a method of identifying a molecule that provides or enhances a sweet taste in the mouth is provided by screening for the effect of a test molecule of on a mammalian cell or cell line that expresses a sulfonylurea receptor (SUR) subunit protein and a potassium inwardly-rectifying channel (Kir) subunit protein via an ATP-gated K+ channel ($K_{ATP}$). In one embodiment, the method involves contacting a test molecule with a mammalian cell or cell line that expresses a sulfonylurea receptor (SUR) subunit protein and a potassium inwardly-rectifying channel (Kir) subunit protein via an ATP-gated K+ channel ($K_{ATP}$) under in vitro culture conditions, and measuring the electrophysiological or functional activity of the $K_{ATP}$ channel in the contacted cell or cell line. A decrease or inhibition in the $K_{ATP}$ electrophysiological or functional activity of the cell or cell line contacted with the test molecule compared to that of a negative control cell or cell line identifies a test molecule that provides or enhances a sweet taste.

In another aspect, a method of identifying a molecule that provides or enhances a sweet taste in the mouth is provided by screening for the effect of a test molecule on the binding or nuclear localization of a SUR1 protein in a cell. In one embodiment, this method involves contacting a test molecule with a mammalian cell or cell line that expresses a sulfonylurea receptor 1 (SUR1) protein under in vitro culture conditions; and detecting binding of the test molecule to the SUR1 protein in the culture. The presence of a significant amount of binding of the test molecule to SUR1 in the cell or cell line contacted with the test molecule over that of a positive or negative control cell or cell line identifies a test molecule that provides or enhances a sweet taste.

In yet another aspect, the use of such test molecules to provide or enhance a sweet taste in the mouth is provided, as are compositions containing such molecules.

Other aspects and advantages of the invention will be readily apparent from the following detailed description of the invention.

BRIEF DESCRIPTION OF THE DRAWINGS

FIG. 1A are gel photomicrographs of PCR amplification (35 cycles) of sugar transporters (GLUT2, GLUT4, GLUT8, GLUT9B and SGLT1), gustducin (GUST, taste RNA control) and GAPDH (tissue RNA control) from mouse cDNA prepared from circumvallate (CV) taste tissue and "non-taste" (NT) lingual epithelial tissue devoid of taste buds. GAPDH is expressed in both cDNA samples; gustducin is expressed only in the taste cDNA. GLUT8, GLUT9B and SGLT1 are more highly expressed in taste cDNA. cDNAs prepared from tissues known to express these genes served as positive controls (CTRL) to confirm the ability of primers to amplify the correct sized product.

FIG. 1B are photomicrographs of PCR amplification (35 cycles) of $K_{ATP}$ subunits (SUR1, SUR2A, SUR2B, Kir6.1, Kir6.2) and insulin receptor (INSR) from mouse cDNA prepared from CV taste tissue and non-taste NT lingual epithelial tissue devoid of taste buds. SUR1, SUR2A, Kir6.1 and INSR are more highly expressed in taste cDNA. cDNAs prepared from tissues known to express these genes served as CTRL to confirm the ability of primers to amplify the correct sized product.

FIG. 1C is a graph showing the results of using Taqman real-time PCR to quantitate expression of sugar transporters, $K_{ATP}$ subunits and insulin receptor in CV (filled bars) taste tissue and NT (gray bars) lingual epithelial tissue devoid of taste buds. Elevated expression in taste cDNA was observed for GLUT8, SGLT1, and insulin receptor. The expression of each gene is plotted as the logarithm of the ratio between its cycle threshold value and that of GAPDH.

FIG. 1D is a graph showing the results of using Taqman real-time PCR to quantitate expression of sugar transporters, $K_{ATP}$ subunits in CV (filled bars) taste tissue and NT (gray bars) lingual epithelial tissue devoid of taste buds. Elevated expression in taste cDNA was observed for GLUT9, SUR1, and Kir6.1. The expression of each gene is plotted as the logarithm of the ratio between its cycle threshold value and that of GAPDH.

DETAILED DESCRIPTION OF THE INVENTION

Figure 1A:
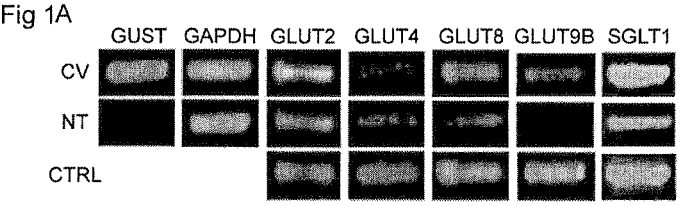
FIG. 1A through FIG. 1D demonstrate the expression of sugar transporter, $K_{ATP}$ glucose sensor and insulin receptor mRNAs in taste tissue.

The methods and compositions described herein provide a means to identify and develop novel sweeteners. Although the combination of type I taste receptors, T1R2 and T1R3, is considered the major receptor underlying sweet taste responses, the inventors have determined significant roles for certain intestinal type sugar transporter proteins and endocrine pancreas type metabolic glucose sensors in sugar (i.e., sweetness) sensing in oral taste cells and thus in the kinetics of sweet taste responses. Without wishing to be bound by theory, the inventors posit that the enhancement of sweet taste by sodium salts depends in part on sodium dependent glucose uptake into taste cells via SGLT1. It is proposed that sweet taste is enhanced by regulating hormone release from T1R3 taste cells in response to sugar responsive changes in taste cell metabolism.

I. Definitions

All scientific and technical terms used herein have their known and normal meaning to a person of skill in the fields of biology, biotechnology and molecular biology and by reference to published texts, which provide one skilled in the art with a general guide to many of the terms used in the present application. However, for clarity, the following terms are particularly defined as follows:

By "providing a sweet taste" is meant that the test molecule alone creates a sweet taste as detected by oral taste cells.

By "enhancing a sweet taste" is meant that the test molecule can increase the sweet taste as detected by oral taste cells of other sweeteners or other composition components, such as a natural sugar, such as glucose or fructose, or an artificial sweetener, such as saccharin, or some other component in a composition for which a sweet taste is desired, e.g., pharmaceuticals and the like.

"Sugar transporter proteins" as used herein, include proteins that function to actively transport, or provide facilitated passive transport within and across cells, of sugars, such as glucose, fructose and others. In one embodiment, a sugar transporter is a sodium-glucose co-transporter (SGLT). In another embodiment, a sugar transporter is a glucose transporter (GLUT). These two families of intestinal sugar transporters are believed to contribute to sweet taste responses of T1R3-containing taste cells. These transporters are theorized to be involved in the kinetics of sweet taste responses, e.g. why artificial sweeteners have delayed onset/offset while carbohydrate sweeteners have rapid onset/offset if they are taken up into taste cells via apical transporters and then metabolized or transported out of taste cells via basolateral sugar transporters. Among important SGLT proteins in the methods described herein are SGLT1 or SGLT3. Among important GLUT family proteins in the methods described herein are GLUT1, GLUT2, GLUT 3, GLUT4, GLUT8, and GLUT9. The nucleotide and/or protein sequences of these sugar transporters are publicly known and may be found, e.g., in GEN-BANK, e.g., murine SGLT1 under Accession No. AAF172491; human SGLT1 Accession No. NP_000334.1; human SGLT3, Accession No. P31636; human GLUT1, Accession No. NP006507.2, murine GLUT1, Accession No. NP0355530.2. Still others are readily available in public databases.

"An ATP-gated K+ channel ($K_{ATP}$)" is a complex of a sulfonylurea receptor (SUR) subunit protein and a potassium inwardly-rectifying (Kir) channel subunit protein. It is found in the cell membrane of pancreatic beta cells and is an endocrine pancreas type sensor of glucose by way of its metabolism to ATP. According to the inventors, $K_{ATP}$ is also involved in T1R-independent sugar sensing in taste cells. When tonically active or activated by another molecule, this channel controls a tonic hyperpolarizing efflux of potassium over the cell membrane. When the channel is inhibited by interaction with certain molecules, the hyperpolarizing efflux is inhibited, thus causing the electrical potential across the membrane to become more positive. In pancreatic endocrine cells, this depolarization opens voltage-gated calcium ion channels, causing a rise in intracellular calcium, which can lead to increased secretion of proinsulin. Similar functions are anticipated to exist in taste cells.

The term "test molecule" as used herein can refer to any known or novel molecule for testing as a sweetener or a molecule to modulate sweetness. Such molecules may typically be found in known libraries of molecules, including those that have been pre-screened e.g., for safe use in animals. Suitable test molecules may be found, for example, in AMES library and may be readily obtained from vendors such as Otava, TimTec, Inc., Chem Bridge Corp., etc. See e.g., Bhal et al, 2007 Mol. Pharmaceutics, 4(4):556-560. The test molecules/compounds identified by the methods of this invention may be chemical compounds, small molecules, nucleic acid sequences, such as cDNAs, or peptides or polypeptides, which provide a sweet taste alone or modulate (increase, enhance, or inhibit, as desired) the sweet taste of other components of a composition.

The term "sulfonylurea compounds" (SU compounds) as used herein refers to molecules having the structure:

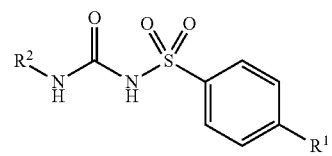

These sulfonylurea derivative compounds contain a center S-phenyl sulfonylurea structure with p-substitution on the phenyl ring ($R^1$) and various groups ($R^2$) terminating the urea N' end group. Sulfonylureas bind to the SUR subunit of the ATP-gated K+ channel ($K_{ATP}$). Desirable sulfonylurea molecules or derivatives for use in the methods and compositions described herein are those derivatives or compounds containing the active moiety above that may be functionally described as binding SUR1, but not increasing pancreatic insulin production. Similarly SUs that do not upregulate non-selective ATP-gated cation channels found in neurovascular tissue are likely desirable compounds. In certain embodiments, known SUs that act topically and are degraded in the gut or resorbed are also likely compounds for use in the methods of this invention. Similarly, SUs that are useful in binding other channel subunits or receptors are likely desirable compounds for enhancing sweetness and may be a group of compounds that are readily identifiable by these methods described herein. In certain embodiments, $R^1$ is halogen, optionally substituted $C_1$ to $C_{10}$ alkyl, optionally substituted $C_3$ to $C_8$ cycloalkyl, optionally substituted aryl, optionally substituted heteroaryl, optionally substituted heterocycle, CN, $NO_2$, optionally substituted $C_2$ to $C_{10}$ alkenyl, optionally substituted $C_2$ to $C_{10}$ alkynyl, OH, $CF_3$, $OCF_3$, $SCF_3$, optionally substituted $C_1$ to $C_{10}$ alkoxy, $CO_2H$, C(O)O (optionally substituted $C_1$ to $C_6$ alkyl), $C(O)NH_2$, C(O)NH (optionally substituted $C_1$ to $C_6$ alkyl), C(O)N (optionally substituted $C_1$ to $C_6$ alkyl) (optionally substituted $C_1$ to $C_6$ alkyl), NHC(O) (optionally substituted $C_1$ to $C_6$ alkyl), NHC(O)O (optionally substituted $C_1$ to $C_6$ alkyl), $NHC(O)NH_2$, NHC(O)NH (optionally substituted $C_1$ to $C_6$ alkyl), $NHSO_2$ (optionally substituted $C_1$ to $C_6$ alkyl), $SO_2$ (optionally substituted $C_1$ to $C_6$ alkyl), $SO_2NH_2$, $SO_2NH$ (optionally substituted $C_1$ to $C_6$ alkyl), or N (optionally substituted $C_1$ to $C_6$ alkyl) (optionally substituted $C_1$ to $C_6$ alkyl).

In certain embodiments, $R^2$ is optionally substituted $C_1$ to $C_{10}$ alkyl, optionally substituted $C_3$ to $C_8$ cycloalkyl, optionally substituted aryl, optionally substituted heteroaryl, optionally substituted heterocycle, optionally substituted $C_2$ to $C_8$ alkenyl, optionally substituted $C_2$ to $C_8$ alkynyl, $CO_2H$, C(O)O (optionally substituted $C_1$ to $C_6$ alkyl), $C(O)NH_2$, C(O)NH (optionally substituted $C_1$ to $C_6$ alkyl), C(O)N (optionally substituted $C_1$ to $C_6$ alkyl) (optionally substituted $C_1$ to $C_6$ alkyl), $SO_2$ (optionally substituted $C_1$ to $C_6$ alkyl), $SO_2NH_2$, $SO_2NH$ (optionally substituted $C_1$ to $C_6$ alkyl), or N (optionally substituted $C_1$ to $C_6$ alkyl) (optionally substituted $C_1$ to $C_6$ alkyl). In some embodiments, $R^2$ is a halogen.

The term "alkyl" is used herein to refer to both straight- and branched-chain saturated aliphatic hydrocarbon groups having 1 to about 10 carbon atoms, and desirably 1 to about 6 carbon atoms (i.e., $C_1$, $C_2$, $C_3$, $C_4$, $C_5$ or $C_6$).

The term "cycloalkyl" is used herein to an alkyl group as just described, but cyclic in structure and having 3 to about 8 carbon atoms. In one embodiment, a cycloalkyl group has 3 to about 8 carbon atoms. In another embodiment, a cycloalkyl group has about 3 to about 6 carbon atoms (i.e., $C_3$, $C_4$, $C_5$ or $C_6$).

The term "alkenyl" is used herein to refer to both straight- and branched-chain alkyl groups having one or more carbon-carbon double bonds and containing about 3 to about 8 carbon atoms. In one embodiment, the term alkenyl refers to an alkyl group having 1 or 2 carbon-carbon double bonds. In a further embodiment, an alkenyl group has about 2 to about 8 carbon atoms. In another embodiment, an alkenyl group has about 2 to about 6 carbon atoms.

The term "alkynyl" is used herein to refer to both straight- and branched-chain alkyl groups having one or more carbon-carbon triple bond and having about 3 to about 8 carbon atoms. In one embodiment, the term alkynyl refers to an alkyl group having 1 or 2 carbon-carbon triple bonds and having about 3 to about 6 carbon atoms.

The term "aryl" as used herein refers to an aromatic system which can include a single ring or multiple aromatic rings fused or linked together where at least one part of the fused or linked rings forms the conjugated aromatic system. The aryl groups include, but are not limited to, phenyl, naphthyl, biphenyl, anthryl, tetrahydronaphthyl, phenanthryl, indene, benzonaphthyl, fluorenyl, and carbazolyl. Desirably, the aryl group is an optionally substituted phenyl group.

The term "heteroaryl," as used herein, refers to an optionally substituted, mono-, di-, tri-, or other multicyclic aromatic ring system that includes at least one, and desirably from 1 to about 4 heteroatom ring members including sulfur, oxygen and nitrogen. In one embodiment, a heteroaryl group can contain about 3 to about 50 carbon atoms, including all combinations and subcombinations of ranges and specific numbers of carbon atoms therein. In another embodiment, a heteroaryl group can contain about 4 to about 10 carbons. Non-limiting examples of heteroaryl groups include, for example, pyrrolyl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl.

The term "heterocyclic" as used herein refers to a stable 4- to 7-membered monocyclic or multicyclic heterocyclic ring which is saturated or partially unsaturated. The heterocyclic ring has in its backbone carbon atoms and one or more heteroatoms including nitrogen, oxygen, and sulfur atoms. Desirably, the heterocyclic ring has 1 to about 4 heteroatoms in the backbone of the ring. When the heterocyclic ring contains nitrogen or sulfur atoms in the backbone of the ring, the nitrogen or sulfur atoms can be oxidized. The term "heterocyclic" also refers to multicyclic rings in which a heterocyclic ring is fused to an aryl ring. The heterocyclic ring can be attached to the aryl ring through a heteroatom or carbon atom provided the resultant heterocyclic ring structure is chemically stable. A variety of heterocyclic groups are known in the art and include, without limitation, oxygen-containing rings, nitrogen-containing rings, sulfur-containing rings, mixed heteroatom-containing rings, fused heteroatom containing rings, and combinations thereof. The heterocyclic groups are selected from, but not limited to, furyl, tetrahydrofuranyl, pyranyl, pyronyl, dioxinyl, pyrrolyl, pyrazolyl, imidazolyl, triazolyl, pyridyl, piperidinyl, 2-oxopiperidinyl, pyridazinyl, pyrimidinyl, pyrazinyl, piperazinyl, azepinyl, triazinyl, pyrrolidinyl, azepinyl, oxathiolyl, oxazolyl, thiazolyl, oxadiazolyl, oxatriazolyl, dioxazolyl, oxathiazolyl, oxathiolyl, oxazinyl, oxathiazinyl, morpholinyl, thiamorpholinyl, thiamorpholinyl sulfoxide, oxepinyl, thiepinyl, diazepinyl, benzofuranyl, thionapthene, indolyl, benazazolyl, purindinyl, pyranopyrrolyl, isoindazolyl, indoxazinyl, benzoxazolyl, anthranilyl, benzopyranyl, quinolinyl, isoquinolinyl, benzodiazonyl, napthylridinyl, benzothienyl, pyridopyridinyl, benzoxazinyl, xanthenyl, acridinyl, and purinyl rings.

The term "alkoxy" as used herein refers to the O(alkyl) group, where the point of attachment is through the oxygen-atom and the alkyl group is optionally substituted.

The term "aryloxy" as used herein refers to the O(aryl) group, where the point of attachment is through the oxygen-atom and the aryl group is optionally substituted.

The term "alkylcarbonyl" as used herein refers to the C(O) (alkyl) group, where the point of attachment is through the carbon-atom of the carbonyl moiety and the alkyl group is optionally substituted.

The term "alkylcarboxy" as used herein refers to the C(O)O(alkyl) group, where the point of attachment is through the carbon-atom of the carboxy moiety and the alkyl group is optionally substituted.

The term "alkylamino" as used herein refers to both secondary and tertiary amines where the point of attachment is through the nitrogen-atom and the alkyl groups are optionally substituted. The alkyl groups can be the same or different.

The term "halogen" as used herein refers to Cl, Br, F, or I groups.

The term "optionally substituted" indicates that the base molecule may be substituted at one or more carbon, nitrogen, oxygen, or sulfur atom, provided that the resulting moiety is chemically stable, with a substituent including, without limitation, halogen, CN, OH, $NO_2$, amino, aryl, heterocycle, alkoxy, aryloxy, alkoxy, alkylcarbonyl, alkylcarboxy, or alkylamino.

The compounds discussed herein also encompass "metabolites" which are unique products formed by processing the compounds of the invention by the cell or subject. Desirably, metabolites are formed in vivo.

"Taste cell", as used herein, refers to a mammalian sensory cell found in taste buds in the oral cavity of mammals, including circumvallate papillae and foliate papillae. These cells can be identified by their typical appearance under light and electron microscopy. They can also be identified by oral location along with expression of taste specific proteins such as alpha-gustducin, T1R1,2,3, T2Rs, TrpM5, Snap25, GLAST.

A "taste-like cell" as used herein refers to any cell outside of the oral cavity that expresses a known taste signaling protein. Such cells include solitary chemosensory cells in the lungs and nose, intestinal endocrine cells, pancreatic endocrine cells and others. Among known taste signaling proteins characteristic of these cells are T1r1, alpha-gustducin, T1r2, T1r3, T2R, and Trpm5.

By use of the term "native cell" is meant a mammalian cell or cell line that naturally or endogenously expresses the indicated mRNA or protein. For example, a native glucose-transporter-expressing oral cell or cell line is a mammalian oral taste cell or oral taste cell line that naturally expresses GLUT.

As used herein, a "heterologous cell or cell line" means a mammalian cell or cell line established from cells that are not oral taste cells, and/or that do not naturally express the desired mRNA or protein. For example, a heterologous cell expressing the glucose-transporter protein may be a human kidney cell (HEK) cell that is genetically engineered to express the desired GLUT protein or a mammalian endocrine cell or cell line that does not naturally express the glucose-transporter protein, but is not an oral cell. In one embodiment, a useful endocrine cell or cell line is an intestinal or gut endocrine cell or cell line. In another embodiment an endocrine cell or cell line is a pancreatic endocrine cell or cell line. Still others are known and useful as provided in the methods described below.

A "transformed cell or cell line" as used herein refers to a mammalian cell or cell line that is genetically engineered to express a desired mRNA or protein that it does not naturally express or that it does not naturally express it in the known amounts. Particularly desirable cells or cell lines are selected from among any mammalian species, including, without limitation, cells such as A549, WEHI, 3T3, 10T1/2, HEK 293 cells, PERC6, Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., epithelial, tumor, etc.

By "expression level" is meant the quantitative expression of the nucleotide sequence (e.g., mRNA) of a desired protein encoding sequence (e.g., sugar-transporter) or the quantitative expression of the desired protein (e.g., sugar-transporter) itself.

By "functional activity" is meant the expected normal activity of a certain mRNA or protein or channel when expressed in a cell. For example, a GLUT protein's functional activity is that of a passive, facilitated transport activity, i.e., the uptake or transport of glucose into a cell or across a cell membrane. For example, an SGLT protein's functional activity is the active uptake and/or co-transport of glucose and sodium into a cell or across a cell membrane. Known assays exist to demonstrate both types of transport and may be used in the methods described below. Examples of suitable assays can be found in Example 1, subparagraph K and in Wilson-O'Brien, Endocrinology, 149(3):917-24 (2008). The functional activity of the $K_{ATP}$ channel is electrophysiological activity, for example the polarization or depolarization of the cell or flux of K+ or other cations, measurable with patch clamp or recording electrodes. For example, see the measure of $K^+$ currents as discussed in Example 4. Another way to measure such activity is by use of indicator dyes that monitor depolarization, e.g., $Ca^{++}$ indicators or specific ion ($K^+$) fluxes.

By "non-specific activity" as used herein is meant an activity induced by a test molecule in a cell culture which is other than active or passive glucose transport or sodium transport, or other than a potassium ion specific channel activity. Non-specific activity can include a test molecule acting in cells that do not express the desired mRNA or protein. Another non-specific activity is inhibiting compounds that normally inhibit the desired functional activity.

By "a counter-screen assay" is meant a known assay that can screen a designated test compound for non-specific activity.

By "mammalian" is meant primarily a human, but also commonly laboratory mammals, such as primates, mice, rats, etc. having native oral cells or taste cells that are capable of discriminating sweet tastes from other tastes.

By "animal physiological or behavioral assays for sweetness" is meant known assays relying on physiological or behavioral reactions in response to increased or decreased sweetness of a compound applied to the oral taste cells of a mammalian test animal or human. Examples of known assays include use of a gustometer (see, e.g., Busch et al, Chem Senses. 2009 May; 34(4):341-8), lickometer (see, e.g., Fudge et al, Horm Behav. 2009 September; 56(3):322-31), conditioned taste aversion (see, e.g., Ayestaran, PLoS One. 2010 Oct. 27; 5(10):e15000), gustatory nerve recording assays (see, e.g., Damak et al, Chem Senses. 2006 March; 31(3): 253-64), and sip and spit taste assays (see, e.g., Delwiche et al, Food Quality and Preference, 1996 March; 7(3-4)293-7). In another embodiment, such assays include electrophysiological responses or calcium imaging or isolated taste cells, isolated taste buds, or taste slices. Other suitable assays are known to those of skill in the art and may be applied in the methods described below.

The terms "a" or "an" refers to one or more, for example, "an assay" is understood to represent one or more assays. As such, the terms "a" (or "an"), "one or more," and "at least one" are used interchangeably herein. As used herein, the term "about" means a variability of 10% from the reference given, unless otherwise specified. While various embodiments in the specification are presented using "comprising" language, under other circumstances, a related embodiment is also intended to be interpreted and described using "consisting of" or "consisting essentially of" language.

II. Specific Methods of the Invention

In one embodiment, a method of identifying a molecule that provides or enhances a sweet taste in the mouth involves contacting a test molecule with a mammalian cell or cell line that expresses a sugar-transporter protein under in vitro culture conditions. Depending upon the specific assay and endpoint desired, suitable culture conditions include a temperature of about 37° C.; or a range of from about 32 to 40° C. This temperature is maintained for about 10 minutes to 24 hours. In some embodiments, the time period is at least about 20 minutes, 30 minutes, 45, minutes, 1 hour, 3 hours, 5 hours, 10 hours, 15 hours, 20 hours or more. The effect of the test molecule on the expression level of the gene product or functional activity of the expressed protein is assessed and quantified by any suitable means as described above for the measurement of expression level.

An increase in protein expression of the sugar-transporter protein or an increase in functional activity of the sugar-transporter protein by the cell or cell line contacted with the test molecule over that of a negative control cell or cell line identifies a test molecule that provides or enhances a sweet taste. That is, the effect of the test molecule to alter the normal expression or activity of the sugar transport protein is related to its impact on providing or enhancing a sweet taste. Where the effect is that the test molecule allows maintenance of normal expression levels or increases levels of the sugar transport protein above those of the controls, that test molecule is indicated to be useful as a potential novel sweetening compound or a compound useful in enhancing the sweetness of other components of an end composition, e.g., foodstuff, medicine, etc. Where the effect is that the test molecule decreases the expression level of the sugar transport protein or decreases its functional activity, the test molecule is indicated to have a potential inhibitory effect on sweet taste when present in a composition.

The negative control used in this method generally is the same cell or cell line contacted by a control molecule, which is known to not provide or enhance a sweet taste in the mouth. In another embodiment, the negative control used in this method generally is the same cell or cell line which is not contacted by a test or control molecule. Thus, the comparison of the effect of the test molecule in the method permits an identification of a result that is correlated with providing or enhancing sweet taste.

Desirably, the cell or cell line used in the method is a native oral taste cell or established oral taste cell line that expresses the sugar transporter protein. In another embodiment, the cell line or cell culture may be a heterologous (non-oral, non-taste) cell or cell line. In still another embodiment the cell or cell line may be a heterologous cell or cell line transformed to express the sugar transporter.

In the performance of this method, the sugar transporter is desirably an SGLT. In one embodiment, the transporter is SGLT 1. In another embodiment, the transporter is SGLT3. Where the SGLT is the sugar transporter expressed, the functional activity is the active co-transport of glucose and sodium.

In another embodiment of this method, the performance of this method, the sugar transporter is desirably a GLUT. In one embodiment, the transporter is GLUT2. In another embodiment, the transporter is GLUT4. In another embodiment, the transporter is GLUT8. In another embodiment, the transporter is GLUT9. In another embodiment, the transporter is GLUT1. In another embodiment, the transporter is GLUT3. In still further embodiments, a combination of GLUT family transporters is expressed and the expression levels and/or functional activities are both measured. Where the GLUT transporter is the sugar transporter expressed, the functional activity is the passive, facilitated transport of glucose.

In still other embodiments, the method is performed to detect and quantify expression of activity of other sugar transporters, e.g., fructose sugar transporters.

In still other embodiments, the method is performed to detect a combination of different sugar transporters, e.g., different GLUTs, or a SLGT and a GLUT, in the same cell or cell line.

The method may further employ a counter-screen assay on the test molecule to exclude non-specific activity of the test molecule in the cell or cell line tested. Additionally, the method may further include screening the test molecule by subjecting the test molecule to an animal physiological response, electrophysiological response, or behavioral assays for sweetness or calcium imaging of isolated taste cells, isolated taste buds or taste slices to confirm that the test molecule provides or enhances a sweet taste.

The examples provided below demonstrate a variety of methods and assays useful in this method.

Another method of identifying a molecule that provides or enhances a sweet taste in the mouth involves contacting a test molecule with a mammalian cell or cell line that expresses a sulfonylurea receptor (SUR, e.g., SUR1) subunit and a potassium inwardly-rectifying channel (Kir, e.g., KIR6.1) subunit via an ATP-gated K+ channel ($K_{ATP}$) under in vitro culture conditions. After suitable culture conditions, e.g., 37° C. for about 10 minutes to 24 hours, as suggested above, the effect of the test molecule on the $K_{ATP}$ functional activity is assessed and quantified by any suitable means.

In one embodiment, the electrophysiological or functional activity of the $K_{ATP}$ channel in the contacted cell or cell line is measured by electrodes. In one embodiment, the electrophysiological activity is a change in certain calcium ion indicators or potassium ion fluxes. In one embodiment, the electrophysiological activity is the polarization or depolarization of the cell or cell line. In one embodiment, the electrophysiological or functional activity of the $K_{ATP}$ channel in the contacted cell or cell line is measured to detect an increase or decrease in the hyperpolarizing efflux of potassium ions over the cell membrane.

For example, a decrease or inhibition in the $K_{ATP}$ electrophysiological or functional activity of the cell or cell line contacted with the test molecule compared to that of a negative control cell or cell line identifies a test molecule that provides or enhances a sweet taste. That is, the effect of the test molecule to alter the normal hyperpolarizing efflux of potassium across the cell membrane is related to providing or enhancing a sweet taste. Where the effect is that the test molecule allows maintenance of normal $K_{ATP}$ channel activity or increased efflux above those of the controls, that effect indicates that the test molecule is not useful as a potential novel sweetening compound. Alternatively, that result indicates that the test molecule has a potential inhibitory effect on sweet taste when present in a composition. Where the effect is that the test molecule decreases the functional activity beyond that of the controls, the test molecule is indicated to be useful in enhancing the sweetness of other components of an end composition, e.g., foodstuff, medicine, etc.

In one embodiment, the negative control used in this method generally is the same cell or cell line contacted by a control molecule, which is known to not provide or enhance a sweet taste in the mouth. In another embodiment, the negative control used in this method generally is the same cell or cell line which is not contacted by a test or control molecule. Thus, the comparison of the effect of the test molecule in the method permits an identification of a result that is correlated with providing or enhancing sweet taste.

Desirably, the cell or cell line used in the method is a native oral taste cell or cell line that expresses the ATP-gated K+ channel. In another embodiment, the cell line or cell culture may be a heterologous (non-oral, non-taste) cell or cell line, e.g., a pancreatic cell or cell line or endocrine cell or cell line. In still another embodiment the cell or cell line may be a heterologous cell or cell line transformed to express the ATP-gated K+ channel.

The method may further employ a counter-screen assay on the test molecule to exclude non-specific activity, e.g., to exclude non-specific $K^+$ electrophysiological activity, mediated by the test molecule in the cell or cell line tested. Additionally, the method may further include screening the test molecule by subjecting the test molecule to an animal physiological response, electrophysiological response, or behavioral assays for sweetness or calcium imaging of isolated taste cells, isolated taste buds or taste slices to confirm that the test molecule provides or enhances a sweet taste.

The examples provided below demonstrate a variety of methods and assays useful in this method.

In another aspect, a method of identifying a molecule that provides or enhances a sweet taste in the mouth involves contacting a test molecule with a mammalian cell or cell line that expresses a sulfonylurea receptor 1 (SUR1) under in vitro culture conditions. After suitable culture conditions as described above in the preceding method, e.g., 37° C. for about 10 minutes to 24 hours, the cell culture is assessed to detect binding of the test molecule to the SUR1 in the culture. Detection of binding may be done by a variety of conventional binding assays. The presence of a significant amount of binding of the test molecule to SUR1 in the cell or cell line contacted with the test molecule over that of a negative control cell or cell line identifies a test molecule that provides or enhances a sweet taste.

According to this method, the negative control comprises the same cell or cell line contacted by a control molecule known to bind SUR1 but not provide or enhance a sweet taste in the mouth. Alternatively, the negative control comprises the same cell or cell line not contacted by a test or control molecule or contacted by a control molecule that does not bind SUR1.

Desirably, in one embodiment, the cell or cell line is an oral taste cell or oral taste cell line. Alternatively, the cell or cell line is a heterologous cell that expresses SUR1. In still another embodiment, the cell or cell line is a transformed cell or cell line that is engineered to express SUR1. In certain embodiments, the cell or cell line is an endocrine cell line, as described above.

In one embodiment, the binding between the test molecule and the SUR1 receptor subunit is detected by a binding assay employing a label bound to the test molecule. Conventional binding assays employing conventional labels may be employed in this assay. Conventional detectable labels may include an enzyme, a fluorochrome, a luminescent or chemi-luminescent material, or a radioactive material. Methods of associating such labels with a test molecule are known to those of skill in the art. Thus to detect SUR1 binding to the test molecule, in one embodiment, the mammalian cell or cell line that expresses SUR1 is contacted with a test molecule or compound that has been labeled with a detectable label. The cells are then washed to remove any non-bound labeled test molecule or compound. The cells are then analyzed to detect the presence of the bound test molecule-SUR1 complex by detecting the detectable label.

The method may further employ a counter-screen assay on the test molecule to exclude non-specific activity, e.g., to exclude non-SUR1 binding activity of the test molecule in the cell or cell line tested. A counter-screen assay is performed concurrently in which the same method steps are performed using a mammalian cell or cell line does not express the SUR1. The counter-screen assay acts as the negative control and allows for the detection of test compounds that bind the expressed SUR1.

Additionally, the method may further include screening the test molecule by subjecting the test molecule to an animal physiological response, electrophysiological response, or behavioral assays for sweetness or calcium imaging of isolated taste cells, isolated taste buds or taste slices to confirm that the test molecule provides or enhances a sweet taste.

The examples provided below demonstrate a variety of methods and assays useful in this method.

Yet another method of identifying a molecule that provides or enhances a sweet taste in the mouth comprises contacting a test molecule with a mammalian cell or cell line that expresses a sulfonylurea receptor (SUR, e.g., SUR1) subunit and a potassium inwardly-rectifying channel (Kir, e.g., KIR6.1) subunit via an ATP-gated K+ channel ($K_{ATP}$) under in vitro culture conditions. After suitable culture conditions, e.g., 37° C. for about 10 minutes to about 24 hours, the effect of the test molecule on the nuclear localization of SUR1 in the contacted cell or cell line is assessed, measured and/or quantified by any suitable means, such as indirect immunofluorescent confocal microscopy as described in Examples 1 and 2. A change in the nuclear localization of SUR1 in the contacted cell or cell line relative to the nuclear localization of SUR1 in a negative control cell or cell line indicates a test molecule that provides or modulates a sweet taste.

In one embodiment, the negative control used in this method generally is the same cell or cell line contacted by a control molecule, which is known to not provide or enhance a sweet taste in the mouth. In another embodiment, the negative control used in this method generally is the same cell or cell line which is not contacted by a test or control molecule. Thus, the comparison of the effect of the test molecule in the method permits an identification of a result that is correlated with providing or enhancing sweet taste.

Desirably, the cell or cell line used in the method is a native oral taste cell or cell line that expresses the ATP-gated K+ channel. In another embodiment, the cell line or cell culture may be a heterologous (non-oral, non-taste) cell or cell line, e.g., a pancreatic cell or cell line or endocrine cell or cell line. In still another embodiment the cell or cell line may be a heterologous cell or cell line transformed to express the ATP-gated K+ channel.

The method may further employ a counter-screen assay on the test molecule to exclude non-specific activity, e.g., to exclude non-specific nuclear localization, or exclude those test molecules with non-desirable properties, mediated by the test molecule in the cell or cell line tested. Additionally, the method may further include screening the test molecule by subjecting the test molecule to an animal physiological response, electrophysiological response, or behavioral assays for sweetness or calcium imaging of isolated taste cells, isolated taste buds or taste slices to confirm that the test molecule provides or enhances a sweet taste.

III. General Methods/Assays Useful in Performance of the Methods

The examples provided below demonstrate a variety of methods and assays useful in this method. Among conventional methods useful in the specified methods above are various means of measuring expression level. The expression level of the gene product may be measured using conventional means including by measurement of protein or nucleic acid. Measurement of the expression level of expressed protein may employ any suitable ligand directed to the expressed protein, e.g., antibody (or antibody to any second biomarker) to detect the protein. Such antibodies may be presently extant in the art or presently used commercially or may be developed by techniques now common in the field of immunology. Similarly, the ligands may be tagged or labeled with reagents capable of providing a detectable signal, depending upon the assay format employed. Such labels are capable, alone or in concert with other compositions or compounds, of providing a detectable signal. Where more than one ligand is employed in a diagnostic method, e.g., such as in a sandwich ELISA, the labels are desirably interactive to produce a detectable signal. Most desirably, the label is detectable visually, e.g. colorimetrically.

Other label systems that may be utilized in the methods of this invention are detectable by other means, e.g., colored latex microparticles (Bangs Laboratories, Indiana) in which a dye is embedded, may be used in place of enzymes to provide a visual signal indicative of the presence of the resulting protein-ligand complex in applicable assays. Still other labels include fluorescent compounds, radioactive compounds or elements. Other reagents for the detection of protein in biological samples, such as peptide mimetics, synthetic chemical compounds capable of detecting SE-CAD may be used in other assay formats for the quantitative detection of SE-CAD protein in biological samples, such as high pressure liquid chromatography (HPLC), immunohistochemistry, etc.

Measurement of the level of the expressed nucleic acid may employ conventional techniques known in the art. Such methods include methods based on hybridization analysis of polynucleotides, methods based on sequencing of polynucleotides, proteomics-based methods or immunochemistry techniques. The most commonly used methods known in the art for the quantification of mRNA expression in a sample include northern blotting and in situ hybridization; RNAse protection assays; and PCR-based methods, such as reverse transcription, real time polymerase chain reaction (RT-PCR) or qPCR. Alternatively, antibodies may be employed that can recognize specific DNA-protein duplexes. The methods described herein are not limited by the particular techniques selected to perform them.

Similarly, any of the methods described herein may employ a high throughput screening assay used to identify test molecules that provide or modulate sweet taste in the mouth. In one embodiment such an assay involves contacting in each individual well of a multi-well plate a different selected test molecule (e.g., nucleotide sequence, amino acid sequence, small molecules, etc) with a mammalian oral cell or cell line that expresses a specific sugar transport protein. In one embodiment that cell is transfected with an expression system (promoter, protein, marker gene) that expresses luciferase (or another marker gene) only when said cell expresses the sugar transport protein. After the compound has been exposed to the expressing cell under appropriate culture conditions, the level of the marker gene (or luminescence) is conventionally measured. A change in the level of expression of the specific sugar transport protein normally expressed by the cell caused by any of the test molecules is correlated with the expression or lack of expression of the marker in each well.

Other conventional assays and techniques also exist for use in the methods described herein, which methods are described in publications referenced herein. Such other assay formats may be used and the assay formats described herein are not a limitation.

A compound which has structural similarity to the test molecules identified herein may also be computationally evaluated and designed by means of a series of steps in which chemical entities or fragments are screened and selected for their ability to associate with or mimic known compounds or test molecules, e.g., known SUs or GLUT-activators or SLGT1 activators, described herein. One skilled in the art may use one of several methods to screen chemical entities or fragments for their ability to mimic the structure of these peptides and more particularly to identify the structure that binds with the SUR1 receptor. This process may begin by visual inspection of, for example, a three dimensional structure on a computer screen. Selected fragments or chemical entities may then be positioned in a variety of orientations to determining structural similarities, or docked, within a putative binding site of the receptor.

Specialized computer programs that may also assist in the process of designing new test molecules based on those identified by the methods herein include the GRID program available from Oxford University, Oxford, UK. (P. J. Goodford, J. Med. Chem., 1985 28:849-857); the MCSS program available from Molecular Simulations, Burlington, Mass. (A. Miranker and M. Karplus, Proteins: Structure, Function and Genetics, 1991 11:29-34); the AUTODOCK program available from Scripps Research Institute, La Jolla, Calif. (D. S. Goodsell and A. J. Olsen, Proteins: Structure, Function, and Genetics, 1990 8:195-202); and the DOCK program available from University of California, San Francisco, Calif. (I. D. Kuntz et al, J. Mol. Biol., 1982 161:269-288), and software such as Quanta and Sybyl, followed by energy minimization and molecular dynamics with standard molecular mechanics force fields, such as CHARMM and AMBER. Additional commercially available computer databases for small molecular compounds include Cambridge Structural Database, Fine Chemical Database, and CONCORD database (for a review see Rusinko, A., 1993, Chem. Des. Auto. News, 8:44-47.

Once suitable chemical entities or fragments have been selected, they can be assembled into a single compound. Assembly may proceed by visual inspection of the relationship of the fragments to each other on the three-dimensional image displayed on a computer screen in relation to the structure of the receptor. Useful programs to aid one of skill in the art in connecting the individual chemical entities or fragments include the CAVEAT program (P. A. Bartlett et at, "CAVEAT: A Program to Facilitate the Structure-Derived Design of Biologically Active Molecules", in Molecular Recognition in Chemical and Biological Problems", Special Pub., Royal Chem. Soc. 78, pp. 182-196 (1989)], which is available from the University of California, Berkeley, Calif.; 3D Database systems such as MACCS-3D database (MDL Information Systems, San Leandro, Calif.) (see, e.g., Y. C. Martin, J. Med. Chem., 1992 35:2145-2154); and the HOOK program, available from Molecular Simulations, Burlington, Mass.

Compounds that mimic a test molecule described herein may be designed as a whole or "de novo" using methods such as the LUDI program (H.-J. Bohm, J. Comp. Aid. Molec. Design, 1992 6:61-78), available from Biosym Technologies, San Diego, Calif.; the LEGEND program (Y. Nishibata and A. Itai, Tetrahedron, 1991 47:8985), available from Molecular Simulations, Burlington, Mass.; and the LeapFrog program, available from Tripos Associates, St. Louis, Mo. Other molecular modeling techniques may also be employed. See, e.g., N. C. Cohen et al, J. Med. Chem., 1990 33:883-894. See also, M. A. Navia and M. A. Murcko, Current Opinions in Structural Biology, 1992 2:202-210. For example, where the structures of test compounds are known, a model of the test compound may be superimposed over the model of the target receptor. Numerous methods and techniques are known in the art for performing this step, any of which may be used. See, e.g., P. S. Farmer, Drug Design, Ariens, E. J., ed., Vol. 10, pp 119-143 (Academic Press, New York, 1980); U.S. Pat. No. 5,331,573; U.S. Pat. No. 5,500,807; C. Verlinde, Structure, 1994 2:577-587; and I. D. Kuntz, Science, 1992 257:1078-1082. The model building techniques and computer evaluation systems described herein are not a limitation.

Thus, using these computer evaluation systems, a large number of compounds may be quickly and easily examined and expensive and lengthy biochemical testing avoided. Moreover, the need for actual synthesis of many compounds is effectively eliminated.

IV. Compositions

Once constructed by the modeling techniques, the proposed new test molecule identified by any of the methods described herein, or a known molecule indicated to have a new use by its identification in these methods may be tested further for bioactivity and compatibility. Such tests are conducted with other components of end compositions using standard techniques, such as the in vitro assay of the examples. Suitable assays for use herein include, but are not limited to, the assays shown below in the examples. Other assay formats may be used and the selection of the assay format is not a limitation of the methods.

For example, in certain embodiments of this invention, the test molecule shown to provide a sweet taste or enhance sweetening is a sulfonylurea (SU) compound or derivative or a peptide or protein have the same three dimensional shape necessary to bind with the SUR1 receptor. For example, sulfonylurea compounds or derivatives that are known to act topically or are degraded in the gut or resorbed provide one class of useful test molecules. Alternatively, SUs that have limited activity to treat diabetes or heart disease are also anticipated to be useful test molecules for compositions of this invention. Similarly derivatives of SUs that are capable of binding other channels or receptors may be similarly useful.

In other embodiments, the test molecule shown to provide a sweet taste or enhance sweetening is a derivative of a known activator of GLUT. Among such known compounds are inhibitors of oxidative phosphylation, such as certain cyanide and azide-like compounds (Shetty et al, 1993 J Biol Chem, 268(23):17225-17232); or TNF alpha, phorbol esters, okadaic acid and 8-bromo-cAMP (Stephens et al 1992 J Biol Chem, 267(12):8336-41); HIF-1 and glucose.

In yet another embodiment, the test molecule shown to provide a sweet taste or enhance sweetening is a derivative of a known activator of SGLT-1, such as isoproterenol or terbutyline (Aschenbach et al, 2002, J. Nutrition, 132:1254-57), lipopolysaccharide or glucose.

The compounds described herein, as well as the sulfonylurea compounds or derivatives, identified as useful by these methods and as described above, may encompass tautomeric forms of the structures provided herein characterized by the bioactivity of the drawn structures. Further, the compounds described herein can be used in the form of salts derived from pharmaceutically or physiologically acceptable acids, bases, alkali metals and alkaline earth metals. Pharmaceutically acceptable salts can be formed from organic and inorganic acids including, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids. Salts may also be formed from inorganic bases, desirably alkali metal salts including, for example, sodium, lithium, or potassium, and organic bases, such as ammonium salts, mono-, di-, and trimethylammonium, mono-, di- and triethylammonium, mono-, di- and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl piperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmonoethanolammonium, and the like.

Physiologically acceptable alkali salts and alkaline earth metal salts can include, without limitation, sodium, potassium, calcium and magnesium salts in the form of esters, and carbamates.

These salts, as well as other compounds described herein can be in the form of esters, carbamates and other conventional "pro-drug" forms, which, when administered in such form, convert to the active moiety in vivo. In one embodiment, the prodrugs are esters. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons (1996).

As described herein, the compounds described herein and/or salts, prodrugs or tautomers thereof, are delivered in regimens therapeutic or prophylactic purposes, as described herein.

The compounds described herein are readily prepared by one of skill in the art from commercially available starting materials or starting materials which can be prepared using literature procedures.

The molecules/compounds discussed above may encompass tautomeric forms of the structures provided herein characterized by the bioactivity of the drawn structures. Further, the compounds may also be used in the form of salts derived from pharmaceutically or physiologically acceptable acids, bases, alkali metals and alkaline earth metals.

The compositions described herein may be formulated neat or with one or more excipient for administration, depending upon the use thereof. One of skill in the art would readily be able to determine suitable additional ingredients to add to such compositions. Not only may the composition be solid or liquid, but may contain additional solid and/or liquid carriers. The carriers may be in dry or liquid form and must be safe for ingestion and/or pharmaceutically acceptable.

The test molecules identified by these methods are useful on their own as sweeteners, in one embodiment. Alternatively, these test molecules are likely to enhance the sweet taste of other known natural or artificial sweeteners, to make such sweeteners more appealing to the human consumer. Still other compositions to which the test molecules may be added include food requiring added sweetness, food additives, beverages, and other products, such as orally administered pharmaceutical products. The compounds of this invention are anticipated to be useful in any composition in which natural or artificial sweeteners are now used (e.g., a sweetener, food additive, beverage, or pharmaceutical product). These compositions (new or known molecules or compounds, identified by the methods above, may be used in any method of providing or modulating a sweet taste in the mouth by contacting mammalian taste cells in vivo with a composition as described above.

The following examples are illustrative only and are not intended to be a limitation on the present invention.

V. EXAMPLES

We examined the nature of T1r-independent sweet taste and observed the presence in taste cells of multiple sugar transporters and sugar sensing molecules other than T1rs. We wanted to determine if taste cells express glucose transporters and metabolic sensors that serve as sugar sensors in other tissues. By RT-PCR, qPCR, in situ hybridization and immunohisto-chemistry, we determined that taste cells do express several glucose transporters (GLUT2, GLUT4, GLUT8 and GLUT9), a sodium-glucose co-transporter (SGLT1), two components of the $K_{ATP}$ metabolic sensor (SUR1 and Kir 6.1) and the insulin receptor were expressed selectively in taste cells. Consistent with a role in sweet taste, GLUT4, SGLT1 and SUR1 were found to be expressed preferentially, selectively or exclusively in T1r3-positive taste cells.

Electrophysiological recording determined that nearly 20% of the total outward current of mouse fungiform taste cells was comprised of sulfonylurea-inhibitable $K_{ATP}$ channels. Because the overwhelming majority of T1r3-expressing taste cells also express SUR1, and vice versa, the inventors posit that $K_{ATP}$ channels constitute a major portion of K+ channels in the T1r3 subset of taste cells. Taste cell-expressed glucose sensors and $K_{ATP}$ thus serve as mediators of the T1r-independent sweet taste of sugars in the sweet-responsive subset of taste cells.

Example 1

Materials and Methods

A. Reagents

Synthetic oligonucleotides were purchased from Genelink (Hawthorne, N.Y.). Kits for plasmid and DNA fragment purification were from Qiagen (Valencia, Calif.). Restriction endonucleases were from New England Biolabs (Beverly, Mass.). Dispase and collagenase A were from Roche (Indianapolis, Ind.). The anti-SNAP-25 antibody was a gift from Dr. Paul Breslin; the anti-SGLT1 antibody was a gift from Dr. Soraya Shirazi-Beechey.

B. Wild Type and Transgenic Mice

All experiments were performed under NIH guidelines for the care and use of animals in research and approved by the Institutional Animal Care and Use Committee of Monell or of Utah State University. All mice used for this study were in the C57BL/6J background. Transgenic mice expressing GFP under promoters for T1r3 (T1r3-GFP) and TrpM5 (TrpM5-GFP) were generated as previously described (Clapp T R et al., 2006).

C. Isolation and Reverse Transcription of Total RNAs

Two adult (2-10 months old) C57BL/6 mice were killed by cervical dislocation and their tongues excised, placed in a PBS solution containing 2 mM EGTA, and the epithelium containing CV papillae was peeled off taking care to minimize contamination from underlying muscle tissue. Non-taste lingual epithelium devoid of taste buds was isolated from the ventral surface of the tongue in a similar way. Total RNA was isolated using the Pure-Link RNA mini kit from Invitrogen (Catalog #12183018A) as per the manufacturer's instructions. Contaminating genomic DNA was digested in column during RNA isolation using Pure-Link DNase (Catalog #12185-010). RNA concentrations were measured using a NanoDrop device (ND-1000, Thermo Scientific). About 500 ng of total RNA was reverse transcribed using SuperScript III First-Strand Synthesis SuperMix for qRT-PCR from Invitrogen (Cat #11752-050).

D. RT-PCR and qPCR

The expression of each gene studied was verified by PCR using PCR SuperMix from Invitrogen (Catalog #10572014). Primers were designed using Primer3 (http://www.ncbi.nlm.nih.gov/tools/primer-blast/). All primer pairs were chosen such that each primer is from a different exon. The primers used for each gene are provided in Table 1.

TABLE 1

RT-PCR Primer Pairs

| Gene Name | Forward Primer | SEQ ID NO. | Reverse Primer | SEQ ID NO. |
|---|---|---|---|---|
| GUSTDUCIN | TGCACCTTAGCCAC TTTCTCCTGGAA | 1 | CCCCTGGGTACGTG CCAAATGA | 2 |
| GAPDH | CCTTCATTGACCTC AACTAC | 3 | GGAAGGCCATGCCA GTGACC | 4 |
| GLUT2 | CGGTGGGACTTGTG CTGCTGG | 5 | GTCTTTTGAGGAAA TCGCTGCAG | 6 |
| GLUT4 | CCTGCCCGAAAGA GTCTAAAGC | 7 | ACTAAGAGCACCGA GACCAACG | 8 |
| GLUT8 | ACTGGTTCATGGCC TTTCTAGTGAC | 9 | CTTAAGAAGGAGAC ACCTGGGTCAG | 10 |
| GLUT9B | GACTCCTACTGCTT CCTCGTCTTC | 11 | GCCAAAGATTAACA ACAGGCATTT | 12 |
| SGLT1 | CTGTACCAACATCG CCTACC | 13 | CCGTTGATGTTCAC CACTGT | 14 |
| SUR1 | AGTGGGAAGTCCT CCTTCTCTCTC | 15 | ACAGTACGAAACAC TAGGCAAGCA | 16 |
| SUR2A | AGTGGAGTGTGAT ACTGGTCCAAAC | 17 | TGGTCTACAGAGTG AGTTCCAGGAC | 18 |
| SUR2B | GATCGCACGGTCGT AACCATAGC | 19 | CAACAGCAAGGTCA TGCTAGTCTT | 20 |
| KIR6.1 | ACCAGAATTCTCTG CGGAAG | 21 | GCCCTGAACTGGTG ATGAGT | 22 |
| KIR6.2 | TTGGAAGGCGTGG TAGAAAC | 23 | GGACAAGGAATCTG GAGAGAT | 24 |
| INSR | ATCTGGATCCCCCT GATAACTGTC | 25 | ACAACAAAATCTTG GTTTGATACGG | 26 |

Reverse Transcriptase (RT)-PCR with GAPDH primers was used to verify successful mRNA isolation and RT reactions. RT-PCR with gustducin primers was used to verify the specificity of taste and non-taste RNAs. cDNAs from tissues where the queried genes were already known to be expressed were used as positive controls. PCR products were separated on 1.5% agarose gels and visualized with ethidium bromide under UV illumination.

Expression of each gene was quantified by qPCR using Taqman Gene Expression (Applied Biosystems) using the FAM dye as reporter, minor groove binder moiety on 5' end, non-fluorescent quencher dye on 3' end, and ROX as passive reference standard. Taqman FAST custom plates were used with GAPDH as internal control and 18s rRNA as manufacturing control. The Taqman probe and primer combinations for each gene were chosen according to the Applied Biosystems website (www.appliedbiosystems.com) and are provided in Table 2.

TABLE 2

TaqMan Probes

| Gene name | Taqman Probe ID No. |
|---|---|
| GUSTDUCIN | Gnat3-Mm01165313_m1 |
| GAPDH | Gapdh-Mm99999915_g1 |
| GLUT4 | Slc2a4-Mm01245502_m1 |
| GLUT8 | Slc2a8-Mm00444634_m1 |
| GLUT9 | Slc2a9-Mm01211147_m1 |
| SGLT1 | Slc5a1-Mm01218040_m1 |
| SUR1 | Abcc8-Mm00803450_m1 |
| SUR2 | Abcc9-Mm00441638_m1 |
| KIR6.1 | Kcnj8-Mm00434620_m1 |
| KIR6.2 | Kcnj11-Mm00440050_s1 |
| INSR | Insr-Mm01211875_m1 |
| T1R3 | Tas1r3-Mm00473459_g1 |
| PKD2L1 | Pkd2l1-Mm00619572_m1 |

A master mix was prepared for CV or NT samples using 2× TaqMan Fast Universal Master Mix (Applied Biosystems, part number: 4444557), nuclease free water and cDNA (0.8 µl/reaction). 10 µl reactions were run in a StepOnePlus machine running StepOne 2.1 software. Each gene was quantified by triplicate reactions in each run and the runs were repeated three times for CV and NT samples from both mice. Data analysis was done using MS Excel. The $\log_{10}$ of average δCt (difference between Ct values of GAPDH and each gene) of each gene was plotted for both CV and NT tissues.

E. RNA Probes

Commercially available mouse Mammalian Gene Collection verified full-length cDNAs for GLUT2 (Slc2a2, clone sequence BC034675.1), GLUT4 (Slc2a4, clone sequence BC014282.1), GLUT9 (Slc2a9, clone sequence BC006076) and SGLT1 (Slc5a1, clone sequence BC003845) were purchased from Open Biosystems (Huntsville, Ala.); SUR1 (Abcc8, clone sequence BC141411.1) was purchased from imaGenes (Berlin, Germany). Each stock was grown in liquid medium and plasmid DNAs purified using a mini-QIAGEN plasmid kit (Valencia, Calif.). Constructs from Open Biosystems were obtained in the pCMV-SPORT6 vector and from imaGenes in the pYX-Asc vector. Plasmid DNA from the above clones were purified using a Quiagen midiprep kit and sequenced by the dye terminator method at the University of Pennsylvania DNA Sequencing Facility using an ABI 96-capillary 3730XL Sequencer. Clone DNAs were digested with SalI and transcribed by T7 or T3 RNA polymerases for anti-sense probes, or digested with NotI and transcribed by Sp6 RNA polymerase for sense probes. Probes were generated with the DIG RNA Labeling kit (Roche, Indianapolis, Ind.) and were purified with ProbeQuant G-50 micro-columns (Amersham Biosciences, Piscataway, N.J.). Concentration and A260/A280 optical density of labeled RNA probes were checked with a NanoDrop reader (ND-1000, Thermo Fisher).

F. Tissue Preparation

Adult male C57BL/6, transgenic T1r3-GFP, and transgenic TrpM5-GFP mice (2-10 months old) were killed by cervical dislocation, then the pancreas, skeletal muscle, small intestine and the circumvallate, foliate and fungiform papillae-containing portions of tongue were quickly removed and briefly rinsed in ice-cold PBS. For in situ hybridization, tissues were freshly frozen in Tissue-Tek O.C.T. mounting media (Sakura, Torrance, Calif.) using a 100% ethanol dry ice bath, then sectioned within 1 hr. For immunohistochemistry, tissues were fixed for 1 hr overnight at 4° C. in 4% paraformaldehyde/1×PBS and cryoprotected in 20% sucrose/1×PBS overnight at 4° C. prior to embedding in O.C.T. Eight to twelve-micron thick sections were prepared using a cryostat CM3050S (Leica Microsystems, Wetzlar, Germany) and applied on precoated microscope slides (Superfrost plus, Fisher Scientific, Pittsburgh, Pa.). The sections were dried at 40° C. for 20 min and immediately used for in situ hybridization or stored at −80° C. for immunohistochemistry.

G. In Situ Hybridization

Fresh sections were fixed for 10 min in 4% paraformaldehyde/1×PBS, permeabilized by a 10 min incubation at 37° C. in 1M Tris-HCl (pH 8.0)/0.5M EDTA containing 10 µg/ml proteinase K (Boehringer Mannheim, Germany), post-fixed for 10 min in 4% paraformaldehyde/1×PBS, then acetylated for 10 min. All steps were followed by three 5 min washes with DEPC-treated 1×PBS. Slides were then prehybridized for 1 hr at room temperature in a mixture containing 50% deionized formamide, 5× saline/sodium citrate (SSC), 5×Denhardts, 500 µg/ml salmon sperm DNA, 250 µl/ml yeast tRNA, 2.5M EDTA in DEPC treated water. For hybridization, aliquots of the mixture were heated at 85° C. for 10 min to denature yeast tRNA and DIG-labeled RNA probe was added to yield desired concentration. The following concentrations were used for each RNA probe: 0.5 µg/ml GLUT2, 0.25 µg/ml GLUT4, 0.25 µg/ml GLUT9, 0.5 µg/ml SGLT1 and 0.3 µg/ml SUR1. The RNA probe mixtures were heated at 85° C. for 3 min to denature the probe then immediately chilled on ice. Hybrislip plastic coverslips (Invitrogen) were used to keep sections from drying out during hybridization and slides were placed in a humidified chamber, sealed in a large moist ziplock bag and incubated at 65° C. overnight. Plastic coverslips were removed by soaking in 5×SSC prewarmed to 65° C. Slides were washed in three times for 30 min each in 0.2×SSC and once for 10 min in PBS with 0.1× TritonX-100 (PBST). A tyramide signal amplification Plus DNP-AP kit (Perkin-Elmer, Boston Mass.) was used according to the manufacturer's protocol to amplify signals from the RNA probes for GLUT2, GLUT4, GLUT9 and SUR1. Slides hybridized with SGLT1 probes displayed significant mRNA labeling in both tongue and intestinal tissues without the amplification steps. These slides were blocked for 1 hr at room temperature with 10% heat inactivated normal goat serum, followed by a 3 hr incubation at room temperature with anti-DIG-alkaline phosphatase (1:1000, Boehringer) in blocking solution. Alkaline phosphate labeling was detected by incubation overnight at room temperature in the dark with a NBT+BICP (nitro blue tetrzolium+5-bromo-4-chloro-3 indolyl-phosphate) mixture (Roche) with levamisole (Sigma, St Louis Mo.). Slides were washed in PBST, rinsed in water, dehydrated with an increasing series of ETOH, cleared with Histoclear (National Diagnostics, Atlanta Ga.), and cover-slipped with Permount (Fisher). Anti-sense and sense RNA probes were used at equivalent concentrations and run in parallel in the same experiment to ensure equivalent conditions. For each experiment in situ hybridization experiment positive controls with T1r3 or gustducin anti-sense probes were done on taste tissue to insure the hybridization worked properly. In addition, in situ hybridization was done on positive control tissues to confirm the quality and specificity of the RNA probes. Anti-sense RNA probes were tested for positive expression in tissues known to express the genes of interest, while sense RNA probes were used as a control. Anti-sense probes demonstrated appropriate expression in pancreas of GLUT2, GLUT9 and SUR1, while sense probes demonstrated low non-specific hybridization in pancreas of GLUT2, GLUT9 and SUR1. Anti-sense probes demonstrated appropriate expression in skeletal muscle of GLUT4, while sense probes demonstrated low non-specific hybridization in skeletal muscle of GLUT4. Anti-sense probes demonstrated appropriate expression in intestines of SGLT1, while sense probes demonstrated low non-specific hybridization in intestines of SGLT1. Data not shown.

H. Immunohistochemistry

Standard immunohistochemical techniques were used. Briefly, frozen sections were rehydrated with PBS. Nonspecific binding was blocked with a blocking buffer (3% bovine serum albumin, 0.3% TritonX-100, 2% goat or donkey serum in 1×PBS) at room temperature for 1-2 hr. Sections were incubated with primary antibody against rabbit anti-GLUT2 (1:150, Santa Cruz Biotechnology, Santa Cruz, sc-9117); rabbit anti-GLUT4 (1:150, Abcam, Cambridge, Mass., ab33780); rabbit anti-Kir6.1 (1:100, Abcam, ab80972); rabbit anti-SGLT1 (1:150, Abcam, ab14686); rabbit anti-SUR1 (1:150, Santa Cruz Biotechnology, sc-25683); goat anti-T1R3 (1:250, Novus Biological, NBP1-46466); goat anti-GLAST1 (1:250, Santa Cruz Biotechnology, sc-7757); or mouse anti-SNAP-25 (1:250, Chemicon, Billerica, Mass., MAB331) overnight at 4° C. in a humidified chamber. After three 15 min washes with PBST, slides were incubated for 1 hr at room temperature with one of the following fluorescent secondary antibodies (1:500) in blocking buffer: Alexa448 donkey anti-rabbit (Molecular Probes, Eugene, Oreg.) for immunofluorescence of rabbit primaries; Alexa594 donkey anti-rabbit (Molecular Probes) for immunofluorescence of rabbit primaries with sections from T1R3-GFP mice. All double immunofluorescent labeling was done with combinations of the following secondaries: Alexa488 donkey anti-goat, Alexa 488 donkey anti-mouse, Alexa594 donkey anti-goat, or Alexa594 donkey anti-rabbit (1:500, Molecular Probes) along with DAPI (1:1000, Molecular Probes) to label cell nuclei. Negative controls included the omission of primary antibody. Glucose transporter antibodies were also tested on positive control tissues. Prior to use with taste bud containing sections all antibodies were tested for positive expression in tissues known to express the genes of interest. Antibodies demonstrated appropriate expression in pancreas: GLUT2, SUR1; skeletal muscle: GLUT4; and small intestine: SGLT1 (Data not shown). Omission of the primary antibody demonstrated low non-specific background from secondary antibodies with these tissues (Data not shown).

I. Imaging

Brightfield images were visualized using a Nikon DXM 1200C digital camera attached to a Nikon Eclipse 80i microscope and captured using Nikon MS-Element F 3.00 software or with a SPOT digital camera (Diagnostic Instruments, Inc) attached to a Nikon SA Microphot microscope and minimally processed using Image-Pro Plus image analysis software (Media Cybernetics Inc., Silver Spring, Md.). Acquisition parameters were held constant for in situ hybridizations with both anti-sense and sense probes. Fluorescent images were captured with the Leica TCS SP2 Spectral Confocal Microscope (Leica Microsystems Inc., Mannheim, Germany) using UV, Ar, GeNe and HeNe lasers and appropriate excitation spectra. Leica Scanware software was used to acquire z-series stacks captured at a 0.25-0.35 µm step size. Images were scanned at a 512×512 pixel format; scan lines were averaged twice and frames scanned three times. Acquisition parameters (i.e., gain, offset, and PMT settings) were held constant for experiments with antibodies and for minus antibody controls. Digital images were cropped and arranged using Photoshop CS (Adobe Systems, Inc., San Jose, Calif.). Related anti-sense and sense images were adjusted at the same brightness and contrast. Fluorescence images within a figure were adjusted for brightness and contrast for background standardization.

J. Cell Counting

Quantitative measurements were conducted to determine the percentage of singly and doubly labeled Type II (T1r3) and Type III (SNAP-25) taste cells that co-expressed GLUT4 or SUR1. Taste bud-containing sections were scanned under a 40× objective on the Lecia confocal microscope and magnified to yield a 100-150 µm$^2$ area in which individual taste cells could be easily distinguished; only those taste cells for which the entire cell bodies could be visualized were counted. For each taste cell type one section of an entire CV papilla and two-three sections from foliate papillae were counted.

K. Sugar Uptake Assay for SGLT-1

Taste cells are incubated with test compounds in cell culture media with low or high glucose for 24 h. Sugar uptake is measured with a radioassay using a $C^{14}$-labeled sugar probe α-MG (Amersham Biosciences, Piscataway, N.J., USA), which is selective for SGLT-1 and is not transported by other glucose transporters (Kimmich & Randles, Am. J. Physiol. 1981 November; 241(5):C227-32; Turner et al., J. Biol. Chem. 1996 Mar. 29; 271(13):7738-44). α-MG uptake is linear from 15 min to at least 2 h. Preliminary studies demonstrate that uptake of the α-MG sugar probe by SGLT-1 is selective using 0.5 mM phloridzin (Sigma) added in the presence of the radiolabeled probe.

Cells are gently washed with glucose-free Hank's balanced salt solution containing 25 mM d-mannitol (mannitol-HBSS) and then incubated with 0.2 ml of mannitol-HBSS containing 2 µCi/ml (6.65 µM) $^{14}$C-labeled α-MG for 30 min at 37° C., 5% $CO_2$ and 96% humidity. Cells are washed with HBSS at 4° C. and solubilized with 0.1 N NaOH. The lysate is mixed into a liquid scintillation cocktail. The level of sugar uptake is measured using a β-scintillation counter. Values are expressed as nanomoles/cm$^2$ surface area.

L. Electrophysiology

Taste buds from the fungiform papillae of wild type C57BL/6 mice were isolated by well established procedures (see, e.g., Baquero A F, Gilbertson T A 2010 *Am J Physiol* doi:10.1152/ajpcell.00318.2010). Individual cells within the taste bud were recorded from using conventional whole cell patch clamp conditions with borosilicate patch pipettes pulled to a resistance of 4-10 MΩ when filled with a standard intracellular solution of K-gluconate, 140 mM; $CaCl_2$, 1 mM; $MgCl_2$, 2 mM; HEPES, 10 mM; EGTA, 11 mM at a pH of 7.2. A nominally $Ca^{2+}$-free extracellular solution containing Na-gluconate, 140 mM; KCl, 5 mM; $MgCl_2$, 1 mM; HEPES, 10 mM, glucose, 10 mM; Na pyruvate, 10 mM, and tetrodotoxin, 0.5 mM was used to isolate outward $K^+$ currents during 0.4 s voltage steps from −80 to +40 mV in 10 mV increments. Glibenclamide (0.1-100 µM; Sigma) was added to this solution and bath-applied at a flow rate of ~4 ml/min permitting solution change in less than 5 s. Series resistance and capacitance were compensated optimally before recording and no records were leak subtracted. Current data were recorded and command potentials delivered using pClamp software (v.8-10). This software was interfaced with an AxoPatch 200B amplifier and Digidata 1322A data acquisition system (Molecular Devices, Sunnyvale, Calif.).

M. Response of Taste Cells to Different Taste Stimuli Determined by Ca-Imaging

Taste cells employed are isolated as described in Example 1 and cultured for a few hours to 1 week or 2 months on rat tail collagen type 1-coated coverslips. See, e.g., Baquero A F, Gilbertson T A 2010 *Am J Physiol* doi:10.1152/ajpce11.00318.2010.

Ca-imaging is performed as follows. The coverslips are incubated for 15-30 minutes with calcium sensitive dye in Modified MHNK ringer's solution (80 mM NaCl, 5 mM KCl, 1 mM $MgCl_2$, 1 mM $CaCl_2$, 1 mM Na-pyruvate, and 20 mM Hepes-Na, pH 7.2 with osmolarity adjusted to 300-310 by 5M NaCl) supplemented with 1 mM Fura-2 AM (Molecular Probes Inc., Eugene, Oreg.) and 20 mg/ml PLURONIC F127 (Molecular Probes Inc.). The calcium sensitive dye fura-2 AM is cleaved to fura-2 which is fluorescent and can be detected.

After incubation, coverslips are placed in a recording chamber and continuously bathed with Modified MHNK Ringer's solution that is applied as superfusion.

The stimuli (Denatonium benzoate 2 mM and 0.5 mM, Acesulfame K 250 ppm, Monosodium glutamate (MSG) 3 mM, Cycloheximide 25 µM, Glycine 125 mM, and High K buffer (modified MHNK ringer's solution with 5 mM NaCl, 80 mM KCl, 1 mM $MgCl_2$, 1 mM $CaCl_2$, 1 mM Na-pyruvate, and 20 mM Hepes-Na, pH 7.2 with osmolarity adjusted to 300-310 by 5M NaCl) are applied to the coverslip by switching the superfusion to the stimulus solution, which allows for a complete change of bath solutions in the chamber within 10 seconds.

Calcium imaging recordings are performed using standard imaging techniques as described by Restrepo D., M. Zviman and N. E. Rawson, "The measurement of intracellular calcium in chemosensory cells", in: Methods in Chemosensory Research, Ed. by A. Spielman and J. Brand. CRC Press, 1995. Illumination is provided by a LSR SPECTRAMASTER monochromator coupled to the microscope. Emitted light from fura-2 in the cells under 200.times. magnification is filtered at 510 nm and recorded with a cooled CCD camera (Olympix, Perkin Elmer Life Sciences, Bethesda Md.). The excitation wavelength is 340-380 nm and the emission wavelength is 510 nm using a wide band filter. Images are digitalized using a Merlin Imaging Workstation (Perkin Elmer Life Sciences, Bethesda Md.), which controls illuminator, camera, and acquisition, and performs the image ratioing and the display of pseudocolor images. After introduction to the recording setup, cells remain viable for over 2 days and can be imaged continuously for 2 hours at a time without visible effects of dye bleaching.

Stimuli are diluted in Modified MHNK ringer's solution and applied via a gravity-flow superfusion apparatus for about 10-60 seconds, depending on the stimulus. Cells can be stimulated by all stimuli tested as shown by a positive signal for Fura-2 AM for at least one cell selected. Typically several cells are tested.

Example 2

Glucose Transporters and Metabolic Sensors are Expressed in Taste Cells

Figure 1B:
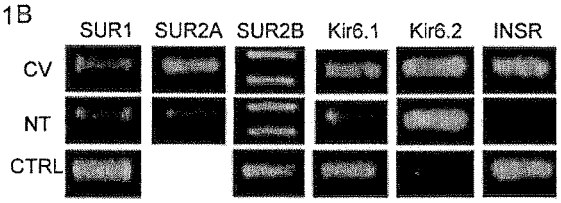

To determine if glucose transporters known to be present in intestine and/or other tissues or metabolic sensors involved in glucose sensing in the pancreas might be present also in taste cells we first examined expression of their mRNAs in taste and non-taste tissues. cDNAs were prepared from taste buds isolated from mouse circumvallate (CV) papillae and from lingual epithelial cells devoid of taste cells ("non-taste" (NT) negative control), then polymerase chain reactions (PCR) were performed using primer pairs specific for cDNAs corresponding to the following: GLUT2, GLUT4, GLUT8, GLUT9B, SGLT1, SUR1, SUR2A, SUR2B, Kir6.1, Kir6.2, and the insulin receptor. By PCR we observed a higher level of expression of GLUT8, GLUT9B, SGLT1, SUR1, SUR2A, Kir 6.1 and the insulin receptor in cDNA from taste than from non-taste tissue (see FIGS. 1A and 1B). PCR indicated that mRNAs for GLUT2, GLUT4 SUR2B and Kir6.2 were not expressed in greater amounts in taste vs. non-taste tissue (FIGS. 1A and 1B).

Figure 1D:
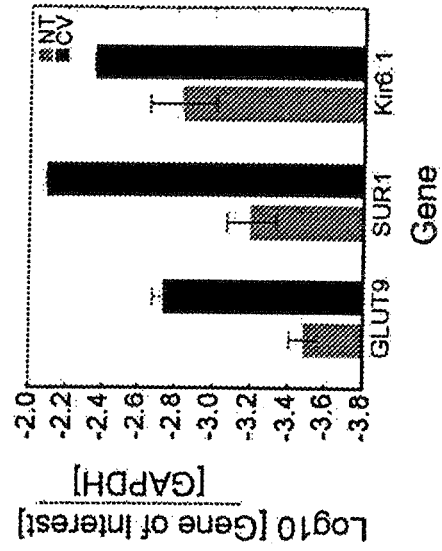
Figure 1C:
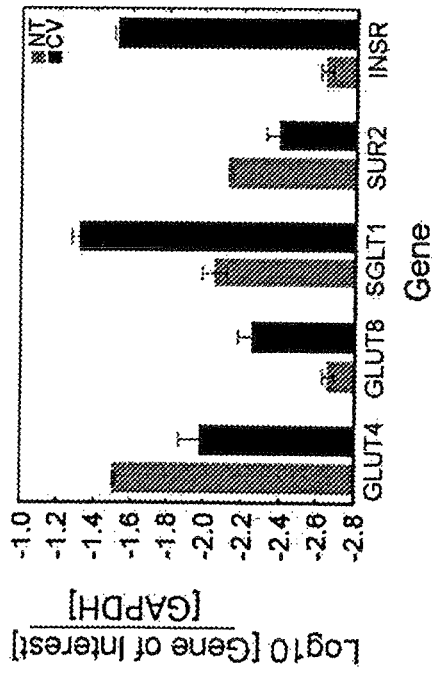

Quantitative evaluation by real-time PCR demonstrated elevated expression in taste tissue cDNA of GLUT8, GLUT9, SGLT1, SUR1, Kir 6.1 and the insulin receptor (FIGS. 1C and 1D). However, GLUT4 and SUR2 were not found by quantitative RT-PCR to be more highly expressed in taste tissue cDNA (FIGS. 1C and 1D). For those genes more highly expressed in taste tissue the absolute levels of mRNA expression in taste tissue were highest for GLUT8, SGLT1 and the insulin receptor. However, the greatest differential expression was found with SUR1 and the insulin receptor: each was ~10-fold more highly expressed in mRNA from taste than from non-taste tissue.

The cDNA templates for the PCR experiments were derived from CV taste tissue containing a mixture of taste cells and surrounding epithelial and connective cells, or control non-taste tissue devoid of taste cells. To determine if the mRNAs for these genes are selectively expressed in the taste cells themselves we carried out in situ hybridization with antisense and sense (control) probes. In situ hybridizations to taste bud containing tissues from mouse circumvallate (CV) and foliate taste papillae were carried out with digoxigenin-labeled RNA probes. In situ hybridization to taste bud-containing sections indicated that mRNAs for GLUT2, GLUT4, GLUT9, SGLT1 and SUR1 are selectively expressed in mouse taste cells in both CV and foliate papillae. Taste cell hybridization to sense probe control in and around taste cells indicative of non-specific background was generally lower than with the corresponding anti-sense probes. Data not shown.

In control experiments each of these probes were validated with tissue sections known to express these mRNAs: GLUT2, GLUT9 and SUR1 in pancreas; GLUT4 in skeletal muscle; SGLT1 in small intestine (Data not shown). Next, immunofluorescence confocal microscopy of taste bud containing sections from mouse circumvallate (CV), foliate and fungiform taste papillae was carried out with specific polyclonal antibodies directed against sugar transporters (GLUT2, GLUT4 and SGLT1) or $K_{ATP}$ subunits (SUR1, Kir6.1). Immunofluorescence that indicates expression in CV cells of GLUT2, GLUT4, SLGT1, SUR1, and Kir6.1 was observed (data not shown). Immunofluorescence that indicates expression in foliate cells of GLUT2, GLUT4, SLGT1, SUR1, and Kir6.1 was observed (data not shown). Immunofluorescence that indicates expression in fungiform cells of GLUT2, GLUT4, SLGT1, SUR1, and Kir6.1 was observed (data not shown).

Immunoreactivity to GLUT2, GLUT4, SGLT1, SUR1 and Kir 6.1 was observed in mouse taste cells of CV, foliate and fungiform papillae (data not shown). Interestingly, much of the SUR1 immunofluorescence appeared to be concentrated within the nucleus of taste cells (data not shown). Indirect immunofluorescence confocal microscopy of taste bud containing sections from mouse circumvallate (CV) and foliate taste papillae was carried out with the nuclear stain DAPI (4',6-diamidino-2-phenylindole) (FIG. 7A, 7 D, 7G) or antibody against the $K_{ATP}$ subunit SUR1. The nuclear pattern of staining of SUR1 was confirmed with DAPI staining (data not shown). Higher magnification indicated that SUR1 was present within the nucleoplasm (data not shown). All primary antibodies were validated for their ability to detect appropriate immunoreactivity in tissues known to express the proteins of interest: GLUT2 and SUR1 in pancreas; GLUT4 in skeletal muscle; SGLT1 in small intestine (data not shown). In addition, secondary antibodies were shown to be free of non-specific immunoreactivity in minus primary controls with pancreas and small intestine (data not shown).

Example 3

GLUT4, SGLT1 and SUR1 are Selectively Expressed in T1r3-Positive Taste Cells

The data above indicate by multiple independent techniques that glucose transporters and $K_{ATP}$ subunits are present in taste cells. Were any of these glucose transporters or sensors of intracellular glucose metabolism to function in taste cell sensing of glucose they would most likely be found in those taste cells that are known to detect glucose and other sweet compounds, i.e. the T1r2+T1r3 positive subset of type II taste cells. To examine this possibility we double stained taste cells using an antibody against a transporter or $K_{ATP}$ subunit along with visualizing the intrinsic fluorescence of green fluorescent protein in the T1r3-expressing taste cells from T1r3-GFP transgenic mice (Clapp T R, et al., 2006). In this way GLUT4, SGLT1 and SUR1 were found to be expressed preferentially in T1r3-positive taste cells. Double staining utilized intrinsic fluorescence of green fluorescent protein (GFP) expressed as a transgene from the T1r3 promoter. Overlaid images indicate frequent co-expression of T1r3 with GLUT4, SGLT1 and SUR1 (data not shown).

Nuclear staining of SUR1 noted above was again observed in taste cells from foliate and circumvallate papillae (data not shown).

Taste cells were doubly stained for GLUT4 and T1r3, SUR1 and T1r3, or SUR1 and SNAP-25, then singly and doubly labeled cells in the circumvallate (A) and foliate (B) taste papillae were counted. The results are recorded in Table 3 below. Numerators are the numbers of taste cells expressing both Gene 1 and Gene 2. Denominators are the numbers of taste cells expressing Gene 1. Taste cells expressing both Gene 1 and Gene 2 as a percentage of those expressing Gene 1 are shown in parentheses. ND, not determined. Quantitation of taste cells that co-express GLUT4 or SUR1 with T1r3 determined that: (1) 90-92% of GLUT4-expressing taste cells express T1r3 while 13-20% of T1r3 cells do not express GLUT4; and (2) 80-85% of SUR1-expressing taste cells express T1r3 while 11-24% of T1r3 cells do not express SUR1. Quantitation of CV taste cells that co-express SUR1 with Snap-25 determined that 17% of SUR1-expressing taste cells express Snap-25. In sum, most SUR1-expressing taste cells are T1r3-expressing Type II cells with the remainder likely being Snap-25-expressing Type III cells.

TABLE 3

Co-expression of GLUT4 and SUR1 with T1R3 or SNAP25 in mouse taste cells

Numbers of circumvallate taste cells expressing one or both genes

| Gene 1 | Gene 2 | | | |
|---|---|---|---|---|
| | GLUT4 | SUR1 | T1r3 | SNAP25 |
| GLUT4 | — | ND | 112/124 (90%) | ND |
| SUR1 | ND | — | 246/307 (80%) | 23/139 (17%) |
| T1r3 | 112/129 (87%) | 246/276 (89%) | — | ND |
| SNAP25 | ND | 23/110 (21%) | ND | — |

TABLE 3-continued

Co-expression of GLUT4 and SUR1 with T1R3 or SNAP25 in mouse taste cells

Numbers of foliate taste cell expressing one or both genes

| Gene 1 | GLUT4 | SUR1 | T1r3 |
|---|---|---|---|
| GLUT4 | — | ND | 113/123 (92%) |
| SUR1 | ND | — | 51/60 (85%) |
| T1r3 | 113/141 (80%) | 51/67 (76%) | — |

Double staining of GLUT4-expressing taste cells with markers for Type I (GLAST) or Type III (Snap-25) taste cells showed that GLUT4 is not present in either taste cell subtype (data not shown). Indirect immunofluorescence confocal microscopy of taste bud containing sections from mouse circumvallate (CV) taste papillae was carried out with antibodies against GLUT4 and SUR1 (data not shown). Double staining was carried out with antibodies to mark Type I taste cells (anti-GLAST), Type III taste cells (anti-SNAP-25) or GFP to mark Type II taste cells (TrpM5-GFP). Overlaid images indicated no co-expression in CV taste cells of GLUT4 with GLAST or SNAP-25, or of SUR1 with GLAST and infrequent co-expression of SUR1 with SNAP-25 (data not shown). In contrast, SUR1 in CV taste cells is mostly in the TrpM5-expressing Type II taste cells (data not shown). Double staining of SUR1-expressing taste cells with markers for Type I, Type II and Type III cells showed that SUR1 is mostly present in Type II (TrpM5) taste cells (data not shown), but not in Type I (GLAST) taste cells (data not shown), and there are a small number of Type III (Snap-25) cells that express SUR1 (data not shown). Preliminary quantitation indicates that (1) most T1r3-expressing Type II taste cells express GLUT4 and SUR1, (2) all GLUT4-expressing taste cells express T1r3, and (3) most SUR1-expressing taste cells express T1r3.

Example 4

Mouse Taste Cells have Functional $K_{ATP}$ Channels

Figure 2A:
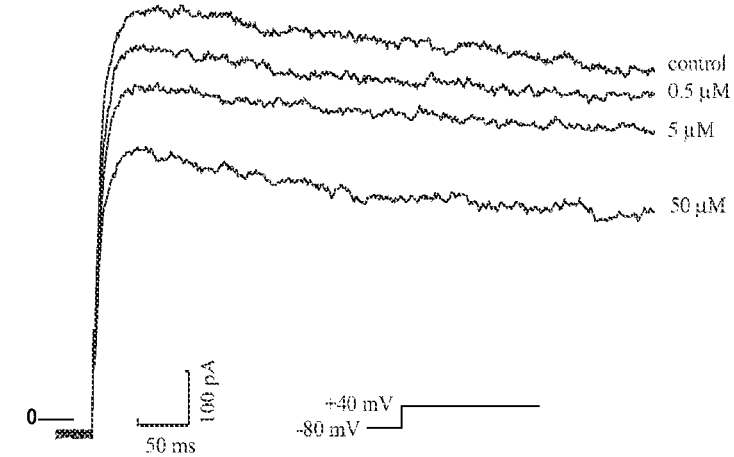
FIG. 2A is a graph showing functional $K_{ATP}$ channels are present in mouse taste cells. Glibenclamide, a sulfonylurea inhibitor of the $K_{ATP}$ channel, inhibits outward ($K^+$) currents in a mouse fungiform taste cell. Each data point is from 7-16 cells.
Figure 2B:
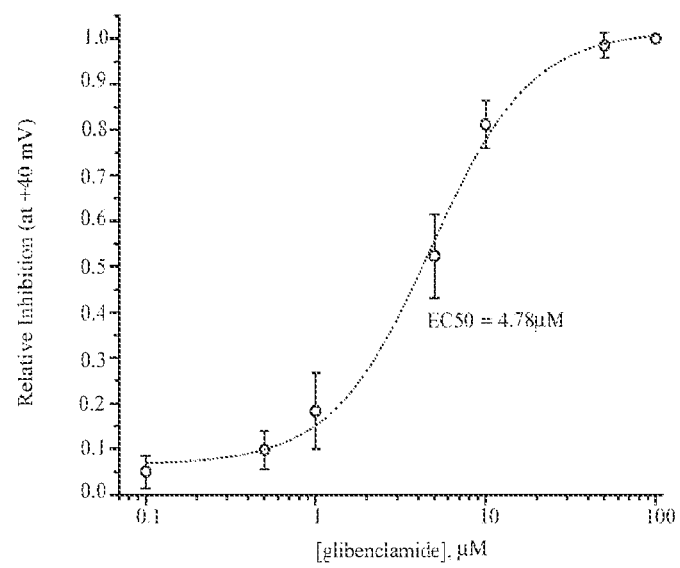
FIG. 2B is a graph showing the concentration-response function for glibenclamide inhibition of outward current (at +40 mV) normalized to the inhibition of the current achieved by application of 100 µM glibenclamide in mouse taste cells. Each data point is from 7-16 cells.

The data derived from the electrophysiology assay described above show that $K_{ATP}$ subunits Kir6.1 and SUR1 are present in taste cells, with SUR1 found mostly in the T1r3-expressing taste cells. Were functional $K_{ATP}$ channels present in mouse taste cells we would expect them to be inhibited by sulfonylurea compounds such as glibenclamide that bind to SUR1. Indeed glibenclamide did inhibit outward ($K^+$) currents in mouse fungiform taste cells (FIGS. 2A and 2B).

Eighteen of 67 taste cells (26.9%) isolated from the fungiform papillae of C57Bl/6 mice showed a significant, reversible inhibition by 20 μM glibenclamide. On average (n=18), 20 μm glibenclamide inhibited 18.70±4.32% of the total outward current in fungiform taste cells, i.e. $K_{ATP}$ channels comprise a significant percentage of total taste cell $K^+$ channels. Given the predominant expression of SUR1 in T1r3 taste cells, an even higher percentage of glibenclamide-inhibitable $K_{ATP}$ channels among total K+ channels would likely be found in T1r3-expressing taste cells.

Without wishing to be bound by theory, the inventors have theorized the following function that $K_{ATP}$ channels play in sweet taste in T1r3-containing taste cells. $K_{ATP}$ channels in pancreas are spontaneously active, as beta cell glucose rises and is metabolized the intracellular ratio of ATP to ADP also rises, leading to $K_{ATP}$ channel closure, depolarization of the cells and insulin release. Our recording of glibenclamide-inhibitable K+ currents was done with a general pool of fungiform taste cells not specifically identified as being T1r3-positive or not. Given that the overwhelming majority of SUR1-expressing taste cells also express T1r3 (and vice versa) it is likely that the sulfonylurea-inhibited $K_{ATP}$ conductance contributes significantly more than 20% of the basal total outward current of T1r3-positive taste cells. $K_{ATP}$ channels in T1r3-containing taste cells could provide a robust means to regulate activity of these cells according to the local content of metabolizable sweet solutions applied to the tongue or the general metabolic state of the organism as communicated to taste cells via blood glucose or circulating hormones. If $K_{ATP}$ channels in T1r3 taste cells are apically disposed then inhibiting this K+ current by sulfonylureas or elevated ATP would depolarize these cells. The combination of a non-caloric sweetener acting via T1r2+T1r3 to initiate a second messenger signaling cascade that depolarizes sweet taste cells along with a caloric sweetener such as glucose that when metabolized promotes closure of T1r3 taste cell $K_{ATP}$ channels would likely provide enhanced perception of sweet taste over that achieved by either sweetener alone.

Conversely, under low glucose/low metabolic conditions the tonic activity of $K_{ATP}$ channels in T1r3 cells would hyperpolarize these taste cells, making it less likely that sweetener activation of T1r2+T1r3 depolarizes the taste cell, thereby opposing sweet perception. Conceivably, regulation of T1r3 cell $K_{ATP}$ channels may be a physiological means to vary taste cell sensitivity to sweet compounds according to metabolic needs. That GLUTs and SGLT1 transporters are co-expressed along with $K_{ATP}$ channels in T1r3-positive taste cells could lead to uptake of sugars via transporters that when metabolized would increase taste cell ATP levels, activate $K_{ATP}$ and hyperpolarize these taste cells. Furthermore, taste cell $K_{ATP}$ might regulate hormone and/or neurotransmitter release from T1r3 taste cells in response to changes in taste cell metabolism. Just as activation of pancreatic beta cell $K_{ATP}$ promotes insulin release so might taste cell $K_{ATP}$ activation promote hormone release from taste cells.

The localization of SUR1 in taste cells to the nucleoplasm is striking and suggests that it is being targeted by a nuclear localization signal or by association with another protein with such a sequence. Previously, SUR1 and functional $K_{ATP}$ channels have been observed in the nuclear envelope of pancreatic beta cells (Quesada, et al. 2002). This nuclear localization in T1r3 taste cells could serve to sequester the sulfonylurea receptor away from the plasma membrane, thereby decreasing the $K_{ATP}$ component of taste cell resting K+ currents or making them insensitive to glibenclamide and other sulfonylureas. Another possibility is that $K_{ATP}$ channels in the nuclear envelope or nucleoplasm affect taste cell transcription of T1r3 itself or other taste signaling components. Such an effect on transcription could alter sweet taste responses over a prolonged period of time and serve to relate taste receptor expression to dietary content.

All publications cited in this specification and U.S. Provisional Patent Application No. 61/435,904, are incorporated herein by reference. While the invention has been described with reference to particular embodiments, it will be appreciated that modifications can be made without departing from the spirit of the invention. Such modifications are intended to fall within the scope of the appended claims.

REFERENCES

1. Amico J A, et al Enhanced initial and sustained intake of sucrose solution in mice with an oxytocin gene deletion. Am J Physiol Regul Integr Comp Physiol. 2005 December; 289(6): R1798-806. Epub 2005 Sep. 8. PubMed PMID: 16150836.
2. Bachmanov A A, Beauchamp G K. Taste receptor genes. Annu Rev Nutr. 2007; 27:389-414. Review. PubMed PMID: 17444812; PubMed Central PMCID: PMC2721271.
3. Bachmanov A A, et al Positional cloning of the mouse saccharin preference (Sac) locus. Chem Senses. 2001 September; 26(7):925-33. PubMed PMID: 11555487.
4. Bachmanov A A, et al Sucrose consumption in mice: major influence of two genetic loci affecting peripheral sensory responses. Mamm Genome. 1997 August; 8(8):545-8. PubMed PMID: 9250857.
5. Baquero A F, Gilbertson T A (2010) Insulin activates epithelial sodium channel (ENaC) via phosphoinositide 3-kinase in mammalian taste receptor cells. *Am J Physiol* doi: 10.1152/ajpcell.00318.2010
6. Bartoshuk L M, et al Taste Of Sodium Chloride Solutions After Adaptation To Sodium Chloride: Implications For The "Water Taste". Science. 1964 Feb. 28; 143:967-8. PubMed PMID: 14090150.
7. Bartoshuk L M, et al Sweet taste of dilute NaCl: psychophysical evidence for a sweet stimulus. Physiol Behav. 1978 October; 21(4):609-13. PubMed PMID: 740780.
8. Clapp T R, et al. Mouse taste cells with G protein-coupled taste receptors lack voltage-gated calcium channels and SNAP-25. BMC Biol. 2006 Mar. 30; 4:7. PubMed PMID: 16573824; PubMed Central PMCID: PMC 1444931.
9. Damak S, et al. Detection of sweet and umami taste in the absence of taste receptor T1r3. Science. 2003 Aug. 8; 301 (5634):850-3. Epub 2003 Jul. 17. PubMed PMID: 12869700.
10. Delay E R, et al. Sucrose and monosodium glutamate taste thresholds and discrimination ability of T1R3 knockout mice. Chem Senses. 2006 May; 31(4):351-7. Epub 2006 Feb. 22. PubMed PMID: 16495435.
11. Desimone J A, et al. The active ion transport properties of canine lingual epithelia in vitro. Implications for gustatory transduction. J Gen Physiol. 1984 May; 83(5):633-56. PubMed PMID: 6330275; PubMed Central PMCID: PMC2215656.
12. DuBois G E, Lee J F. A simple technique for the evaluation of temporal taste properties. Chem. Senses. 1983 7 (3-4): 237-247.
13. DuBois G E, et al. Concentration-response relationships of sweeteners: A systematic study. In: Walters D E, et al, eds. Sweeteners: Discovery, molecular design, and chemoreception. ACS Symposium Series 450. Washington, D.C. American Chemical Society: 1991: 261-276.
14. Fuller J L. Single-locus control of saccharin preference in mice. J Hered. 1974 January-February; 65(1):33-6. PubMed PMID: 4847746.
15. Fushan A A, et al. Association between common variation in genes encoding sweet taste signaling components and human sucrose perception. Chem Senses. 2010 September; 35(7):579-92. Epub 2010 Jul. 21. PubMed PMID: 20660057; PubMed Central PMCID: PMC2924427.
16. Fushan A A, et al. Allelic polymorphism within the TAS1R3 promoter is associated with human taste sensitivity to sucrose. Curr Biol. 2009 Aug. 11; 19(15):1288-93. Epub 2009 Jun. 25. PubMed PMID: 19559618; PubMed Central PMCID: PMC2742917.
17. Hevezi P, et al. Genome-wide analysis of gene expression in primate taste buds reveals links to diverse processes. PLoS One. 2009 Jul. 28; 4(7):e6395. PubMed PMID: 19636377; PubMed Central PMCID: PMC2712080.

18. Jiang P, et al. Lactisole interacts with the transmembrane domains of human T1R3 to inhibit sweet taste. J Biol Chem. 2005 Apr. 15; 280(15):15238-46. Epub 2005 Jan. 24. PubMed PMID: 15668251.
19. Jiang P, et al. The cysteine-rich region of T1R3 determines responses to intensely sweet proteins. J Biol Chem. 2004 Oct. 22; 279(43):45068-75. Epub 2004 Aug. 6. PubMed PMID: 15299024.
20. Jyotaki M, et al. Modulation of sweet taste sensitivity by orexigenic and anorexigenic factors. Endocr J. 2010; 57(6):467-75. Epub 2010 Apr. 23. Review. PubMed PMID: 20431269.
21. Keskitalo K, et al. Sweet taste preferences are partly genetically determined: identification of a trait locus on chromosome 16. Am J Clin Nutr. 2007 July; 86(1):55-63. PubMed PMID: 17616763.
22. Kinnamon, S. C. and Margolskee, R. F. (2008) Taste Transduction. The Senses: A Comprehensive Reference. Ed R. R. Hoy, G. M Shepherd, A. I. Basbaum, A. Kaneko and G. Westheimer. Vol. 2.
23. Kitagawa M, et al. Molecular genetic identification of a candidate receptor gene for sweet taste. Biochem Biophys Res Commun. 2001 Apr. 27; 283(1):236-42. PubMed PMID: 11322794.
24. Kumazawa T, Kurihara K. Large enhancement of canine taste responses to sugars by salts. J Gen Physiol. 1990 May; 95(5):1007-18. PubMed PMID: 2362181; PubMed Central PMCID: PMC2216347.
25. Li X, et al. Human receptors for sweet and umami taste. Proc Natl Acad Sci USA. 2002 Apr. 2; 99(7):4692-6. Epub 2002 Mar. 26. PubMed PMID: 11917125; PubMed Central PMCID: PMC123709.
26. Liu D X, et al. Expression of sulfonylurea receptors in rat taste buds. Acta Histochem. 2010 Jun. 30. [Epub ahead of print] PubMed PMID: 20598356.
27. Max M, et al. Tas1r3, encoding a new candidate taste receptor, is allelic to the sweet responsiveness locus Sac. Nat Genet. 2001 May; 28(1):58-63. PubMed PMID: 11326277.
28. McTaggart J S, et al. The role of the KATP channel in glucose homeostasis in health and disease: more than meets the islet. J Physiol. 2010 Sep. 1; 588(Pt 17):3201-9. Epub 2010 Jun. 2. PubMed PMID: 20519313; PubMed Central PMCID: PMC2976015.
29. Mierson S, et al. Sugar-activated ion transport in canine lingual epithelium. Implications for sugar taste transduction. J Gen Physiol. 1988 July; 92(1):87-111. PubMed PMID: 3171536; PubMed Central PMCID: PMC2228888.
30. Montmayeur J P, et al. A candidate taste receptor gene near a sweet taste locus. Nat Neurosci. 2001 May; 4(5): 492-8. PubMed PMID: 11319557.
31. Nelson G, et al. Mammalian sweet taste receptors. Cell. 2001 Aug. 10; 106(3):381-90. PubMed PMID: 11509186.
32. Nichols C G. KATP channels as molecular sensors of cellular metabolism. Nature. 2006 Mar. 23; 440(7083): 470-6. Review. PubMed PMID: 16554807.
33. Pelz W E, et al. Genetic influences on saccharin preference of mice. Physiol Behav. 1973 February; 10(2):263-5. PubMed PMID: 4708496.
34. Quesada I, et al. Nuclear KATP channels trigger nuclear Ca(2+) transients that modulate nuclear function. Proc Natl Acad Sci USA. 2002 Jul. 9; 99(14):9544-9. Epub 2002 Jun. 27. PubMed PMID: 12089327; PubMed Central PMCID: PMC 123177.
35. Reed D R, et al. Heritable variation in food preferences and their contribution to obesity. Behav Genet. 1997 July; 27(4):373-87. Review. PubMed PMID: 9519563.
36. Sainz E, et al. Identification of a novel member of the T1R family of putative taste receptors. J Neurochem. 2001 May; 77(3):896-903. PubMed PMID: 11331418.
37. Scheepers A, et al. The glucose transporter families SGLT and GLUT: molecular basis of normal and aberrant function. JPEN J Parenter Enteral Nutr. 2004 September-October; 28(5):364-71. Review. PubMed PMID: 15449578.
38. Schiffman S S, et al. Multiple receptor sites mediate sweetness: evidence from cross adaptation. Pharmacol Biochem Behav. 1981 September; 15(3):377-88. PubMed PMID: 7291240.
39. Sclafani A, et al. Oxytocin knockout mice demonstrate enhanced intake of sweet and nonsweet carbohydrate solutions. Am J Physiol Regul Integr Comp Physiol. 2007 May; 292(5):R1828-33. Epub 2007 Feb. 1. PubMed PMID: 17272659; PubMed Central PMCID: PMC2360481.
40. Shigemura N, et al. Leptin modulates behavioral responses to sweet substances by influencing peripheral taste structures. Endocrinology. 2004 February; 145(2): 839-47. Epub 2003 Oct. 30. PubMed PMID: 14592964.
41. Shin Y K, et al. Modulation of taste sensitivity by GLP-1 signaling. J Neurochem. 2008 July; 106(1):455-63. Epub 2008 Jul. 1. PubMed PMID: 18397368; PubMed Central PMCID: PMC2629996.
42. Simon S A, et al. Activation by saccharides of a cation-selective pathway on canine lingual epithelium. Am J Physiol. 1989 February; 256(2 Pt 2):R394-402. PubMed PMID: 2916696.
43. Simon S A. (1991) Mechanisms of Sweet Taste Transduction in Sweeteners, ACS Symposium Series, Vol. 450, pp 237-250.
44. Ugawa T, et al. Enhancing effects of NaCl and Na phosphate on human gustatory responses to amino acids. Chem Senses 1992 17 (6): 811-815.
45. Winnig M, et al. Valine 738 and lysine 735 in the fifth transmembrane domain of rTas1r3 mediate insensitivity towards lactisole of the rat sweet taste receptor. BMC Neurosci. 2005 Apr. 7; 6:22. PubMed PMID: 15817126; PubMed Central PMCID: PMC 1084349.
46. Xu H, et al. Different functional roles of T1R subunits in the heteromeric taste receptors. Proc Natl Acad Sci USA. 2004 Sep. 28; 101(39):14258-63. Epub 2004 Sep. 7. PubMed PMID: 15353592; PubMed Central PMCID: PMC521102.
47. Yoshida R, et al. Endocannabinoids selectively enhance sweet taste. Proc Natl Acad Sci USA. 2010 Jan. 12; 107 (2):935-9. Epub 2009 Dec. 22. PubMed PMID: 20080779; PubMed Central PMCID: PMC2818929.
48. Zhao F Q, Keating A F. Functional properties and genomics of glucose transporters. Curr Genomics. 2007 April; 8(2):113-28. PubMed PMID: 18660845; PubMed Central PMCID: PMC2435356.
49. Zhao G Q, et al. The receptors for mammalian sweet and umami taste. Cell. 2003 Oct. 31; 115(3):255-66. PubMed PMID: 14636554.

What is claimed is:

1. A method of identifying a molecule that provides or enhances a sweet taste in the mouth comprising:
   (a) contacting a test molecule with a mammalian cell or cell line that expresses a sulfonylurea receptor 1 (SUR1) and a potassium inwardly-rectifying channel (Kir) via an ATP-gated K+ channel ($K_{ATP}$) under in vitro culture conditions; and either
   (b)(i) measuring the electrophysiological or functional activity of the $K_{ATP}$ channel in the contacted cell or cell line; wherein a decrease or inhibition in the $K_{ATP}$ electrophysiological or functional activity of the cell or cell line contacted with the test molecule compared to that of a negative control identifies a test molecule that provides or enhances a sweet taste; or
   (b)(ii) measuring or detecting the nuclear localization of SUR1 in the contacted cell or cell line; wherein a change in the nuclear localization of SUR1 in the contacted cell or cell line relative to the nuclear localization of SUR1 in the negative control indicates a test molecule that provides or modulates a sweet taste;
   wherein the negative control is the same mammalian cell or cell line contacted by a control molecule known to not provide or enhance a sweet taste in the mouth; or the same cell or cell line not contacted by a test or control molecule.

2. The method according to claim 1, wherein the Kir is KIR6.1.

3. The method according to claim 1, wherein the cell or cell line is an oral taste cell or oral taste cell line, a heterologous cell that expresses the $K_{ATP}$ channel, a transformed cell or cell line that is engineered to express the $K_{ATP}$ channel or an endocrine cell or cell line that is engineered to express the $K_{ATP}$ channel.

4. The method according to claim 1, wherein the electrophysiological activity is the polarization or depolarization of the cell or cell line or a change in certain ion indicators or fluxes.

5. The method according to claim 1, further comprising one or more of the following:
   (c) performing a counter-screen assay on the test molecule to exclude non-specific K+ electrophysiological activity mediated by the test molecule;
   (d) performing a counter-screen assay on the test molecule to exclude non-specific nuclear localization mediated by the test molecule; and
   (e) subjecting the test molecule to an animal physiological response assay, an electrophysiological response assay, or a behavioral assay for sweetness, or a calcium imaging of isolated taste cells, isolated taste buds or taste slices.

6. A method of identifying a molecule that provides or enhances a sweet taste in the mouth comprising:
   (a) contacting a test molecule with a mammalian cell or cell line that expresses a sugar-transporter selected from SGLT1 and GLUT4 under in vitro culture conditions; and
   (b) measuring the expression level or functional activity of the sugar-transporter by the contacted cell or cell line; wherein an increase in expression of the sugar-transporter or functional activity of the sugar-transporter by the cell or cell line contacted with the test molecule over that of a negative control cell or cell line identifies a test molecule that provides or enhances a sweet taste.

7. The method according to claim 6, wherein the expression level is the level of sugar-transporter mRNA or protein.

8. The method according to claim 6, wherein the sugar-transporter-expressing cell or cell line is an oral taste cell or oral taste cell line, a heterologous cell, a transformed cell or cell line that is engineered to express sugar-transporter, an endocrine cell or cell line or any cell or cell line that expresses a taste signaling protein.

9. The method according to claim 6, wherein the functional activity is selected from: an active transport activity, a passive, facilitated transport activity, the uptake or transport of glucose and the uptake or transport of sodium.

10. The method according to claim 6, further comprising one or more of the following:
    (c) performing a counter-screen assay on the test molecule to exclude non-specific activity of the test molecule; and
    (d) subjecting the test molecule to an animal physiological response assay, an electrophysiological response assay, a behavioral assay for sweetness, or a calcium imaging of isolated taste cells, isolated taste buds or taste slices.

11. The method according to claim 6, wherein the negative control comprises the same cell or cell line contacted by a control molecule known to not provide or enhance a sweet taste in the mouth; or the same cell or cell line not contacted by a test or control molecule.

12. A method of identifying a molecule that provides or enhances a sweet taste in the mouth comprising:
    (a) contacting a test molecule with a mammalian cell or cell line that expresses a sulfonylurea receptor 1 (SUR1) protein under in vitro culture conditions; and
    (b) detecting binding of the test molecule to the SUR1 protein in the culture; wherein the presence of a significant amount of binding of the test molecule to SUR1 in the cell or cell line contacted with the test molecule over that of a negative control cell or cell line identifies a test molecule that provides or enhances a sweet taste.

13. The method according to claim 12, wherein the binding is detected by a binding assay employing a label bound to the test molecule.

14. The method according to claim 12, further comprising one or more of the following:
    (c) performing a counter-screen assay on the test molecule to exclude non-SUR1 binding activity of the test molecule; and
    (d) subjecting the test molecule to an animal physiological response assay, an electrophysiological response assay, a behavioral assay for sweetness, or a calcium imaging of isolated taste cells, isolated taste buds or taste slices.

15. The method according to claim 12, wherein the negative control comprises the same cell or cell line contacted by a control molecule known to bind SUR1 but not provide or enhance a sweet taste in the mouth; or the same cell or cell line not contacted by a test or control molecule or contracted by a control molecule that does not bind SUR1.

* * * * *

SEQUENCE LISTING

<160> NUMBER OF SEQ ID NOS: 26

<210> SEQ ID NO 1
<211> LENGTH: 26
<212> TYPE: DNA
<213> ORGANISM: Artificial Sequence
<220> FEATURE:
<223> OTHER INFORMATION: forward primer based on Mus musculus

<400> SEQUENCE: 1
tgcaccttag ccactttctc ctggaa                                          26

<210> SEQ ID NO 2
<211> LENGTH: 22
<212> TYPE: DNA
<213> ORGANISM: Artificial Sequence
<220> FEATURE:
<223> OTHER INFORMATION: reverse primer based on Mus musculus

<400> SEQUENCE: 2
cccctgggta cgtgccaaat ga                                              22

<210> SEQ ID NO 3
<211> LENGTH: 20
<212> TYPE: DNA
<213> ORGANISM: Artificial Sequence
<220> FEATURE:
<223> OTHER INFORMATION: forward primer based on Mus musculus

<400> SEQUENCE: 3
ccttcattga cctcaactac                                                 20

<210> SEQ ID NO 4
<211> LENGTH: 20
<212> TYPE: DNA
<213> ORGANISM: Artificial Sequence
<220> FEATURE:
<223> OTHER INFORMATION: reverse primer based on Mus musculus

<400> SEQUENCE: 4
ggaaggccat gccagtgacc                                                 20

<210> SEQ ID NO 5
<211> LENGTH: 21
<212> TYPE: DNA
<213> ORGANISM: Artificial Sequence
<220> FEATURE:
<223> OTHER INFORMATION: forward primer based on Mus musculus

<400> SEQUENCE: 5
cggtgggact tgtgctgctg g                                               21

<210> SEQ ID NO 6
<211> LENGTH: 23
<212> TYPE: DNA
<213> ORGANISM: Artificial Sequence
<220> FEATURE:
<223> OTHER INFORMATION: reverse primer based on Mus musculus

<400> SEQUENCE: 6
gtcttttgag gaaatcgctg cag                                             23

<210> SEQ ID NO 7
<211> LENGTH: 22
<212> TYPE: DNA
<213> ORGANISM: Artificial Sequence

```
<220> FEATURE:
<223> OTHER INFORMATION: forward primer based on Mus musculus

<400> SEQUENCE: 7
cctgcccgaa agagtctaaa gc                                              22

<210> SEQ ID NO 8
<211> LENGTH: 22
<212> TYPE: DNA
<213> ORGANISM: Artificial Sequence
<220> FEATURE:
<223> OTHER INFORMATION: reverse primer based on Mus musculus

<400> SEQUENCE: 8
actaagagca ccgagaccaa cg                                              22

<210> SEQ ID NO 9
<211> LENGTH: 25
<212> TYPE: DNA
<213> ORGANISM: Artificial Sequence
<220> FEATURE:
<223> OTHER INFORMATION: forward primer based on Mus musculus

<400> SEQUENCE: 9
actggttcat ggcctttcta gtgac                                           25

<210> SEQ ID NO 10
<211> LENGTH: 25
<212> TYPE: DNA
<213> ORGANISM: Artificial Sequence
<220> FEATURE:
<223> OTHER INFORMATION: reverse primer based on Mus musculus

<400> SEQUENCE: 10
cttaagaagg agacacctgg gtcag                                           25

<210> SEQ ID NO 11
<211> LENGTH: 24
<212> TYPE: DNA
<213> ORGANISM: Artificial Sequence
<220> FEATURE:
<223> OTHER INFORMATION: forward primer based on Mus musculus

<400> SEQUENCE: 11
gactcctact gcttcctcgt cttc                                            24

<210> SEQ ID NO 12
<211> LENGTH: 24
<212> TYPE: DNA
<213> ORGANISM: Artificial Sequence
<220> FEATURE:
<223> OTHER INFORMATION: reverse primer based on Mus musculus

<400> SEQUENCE: 12
gccaaagatt aacaacaggc attt                                            24

<210> SEQ ID NO 13
<211> LENGTH: 20
<212> TYPE: DNA
<213> ORGANISM: Artificial Sequence
<220> FEATURE:
<223> OTHER INFORMATION: forward primer based on Mus musculus

<400> SEQUENCE: 13
ctgtaccaac atcgcctacc                                                 20
```

-continued

```
<210> SEQ ID NO 14
<211> LENGTH: 20
<212> TYPE: DNA
<213> ORGANISM: Artificial Sequence
<220> FEATURE:
<223> OTHER INFORMATION: reverse primer based on Mus musculus

<400> SEQUENCE: 14
ccgttgatgt tcaccactgt                                                   20

<210> SEQ ID NO 15
<211> LENGTH: 24
<212> TYPE: DNA
<213> ORGANISM: Artificial Sequence
<220> FEATURE:
<223> OTHER INFORMATION: forward primer based on Mus musculus

<400> SEQUENCE: 15
agtgggaagt cctccttctc tctc                                              24

<210> SEQ ID NO 16
<211> LENGTH: 24
<212> TYPE: DNA
<213> ORGANISM: Artificial Sequence
<220> FEATURE:
<223> OTHER INFORMATION: reverse primer based on Mus musculus

<400> SEQUENCE: 16
acagtacgaa acactaggca agca                                              24

<210> SEQ ID NO 17
<211> LENGTH: 25
<212> TYPE: DNA
<213> ORGANISM: Artificial Sequence
<220> FEATURE:
<223> OTHER INFORMATION: forward primer based on Mus musculus

<400> SEQUENCE: 17
agtggagtgt gatactggtc caaac                                             25

<210> SEQ ID NO 18
<211> LENGTH: 25
<212> TYPE: DNA
<213> ORGANISM: Artificial Sequence
<220> FEATURE:
<223> OTHER INFORMATION: reverse primer based on Mus musculus

<400> SEQUENCE: 18
tggtctacag agtgagttcc aggac                                             25

<210> SEQ ID NO 19
<211> LENGTH: 23
<212> TYPE: DNA
<213> ORGANISM: Artificial Sequence
<220> FEATURE:
<223> OTHER INFORMATION: forward primer based on Mus musculus

<400> SEQUENCE: 19
gatcgcacgg tcgtaaccat agc                                               23

<210> SEQ ID NO 20
<211> LENGTH: 24
<212> TYPE: DNA
<213> ORGANISM: Artificial Sequence
<220> FEATURE:
<223> OTHER INFORMATION: reverse primer based on Mus musculus
```

<400> SEQUENCE: 20
caacagcaag gtcatgctag tctt                                        24

<210> SEQ ID NO 21
<211> LENGTH: 20
<212> TYPE: DNA
<213> ORGANISM: Artificial Sequence
<220> FEATURE:
<223> OTHER INFORMATION: forward primer based on Mus musculus

<400> SEQUENCE: 21
accagaattc tctgcggaag                                             20

<210> SEQ ID NO 22
<211> LENGTH: 20
<212> TYPE: DNA
<213> ORGANISM: Artificial Sequence
<220> FEATURE:
<223> OTHER INFORMATION: reverse primer based on Mus musculus

<400> SEQUENCE: 22
gccctgaact ggtgatgagt                                             20

<210> SEQ ID NO 23
<211> LENGTH: 20
<212> TYPE: DNA
<213> ORGANISM: Artificial Sequence
<220> FEATURE:
<223> OTHER INFORMATION: forward primer based on Mus musculus

<400> SEQUENCE: 23
ttggaaggcg tggtagaaac                                             20

<210> SEQ ID NO 24
<211> LENGTH: 21
<212> TYPE: DNA
<213> ORGANISM: Artificial Sequence
<220> FEATURE:
<223> OTHER INFORMATION: reverse primer based on Mus musculus

<400> SEQUENCE: 24
ggacaaggaa tctggagaga t                                           21

<210> SEQ ID NO 25
<211> LENGTH: 24
<212> TYPE: DNA
<213> ORGANISM: Artificial Sequence
<220> FEATURE:
<223> OTHER INFORMATION: forward primer based on Mus musculus

<400> SEQUENCE: 25
atctggatcc ccctgataac tgtc                                        24

<210> SEQ ID NO 26
<211> LENGTH: 25
<212> TYPE: DNA
<213> ORGANISM: Artificial Sequence
<220> FEATURE:
<223> OTHER INFORMATION: reverse primer based on Mus musculus

<400> SEQUENCE: 26
acaacaaaat cttggtttga tacgg                                       25